US006743920B2

(12) United States Patent
Lindstrom et al.

(10) Patent No.: US 6,743,920 B2
(45) Date of Patent: Jun. 1, 2004

(54) PROCESS FOR IMIDAZO[4,5-C]PYRIDIN-4-AMINES

(75) Inventors: Kyle J. Lindstrom, Houlton, WI (US); Luke T. Dressel, Somerset, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/436,488

(22) Filed: May 12, 2003

(65) Prior Publication Data

US 2003/0232852 A1 Dec. 18, 2003

Related U.S. Application Data

(60) Provisional application No. 60/384,558, filed on May 29, 2002.

(51) Int. Cl.⁷ .............................................. C07D 471/02
(52) U.S. Cl. ...................................................... 546/118
(58) Field of Search ......................................... 546/118

(56) References Cited

U.S. PATENT DOCUMENTS 4,689,338 A    8/1987   Gerster
4,929,624 A    5/1990   Gerster et al.
4,988,815 A    1/1991   Andre et al.
5,175,296 A   12/1992   Gerster
5,367,076 A   11/1994   Gerster
5,395,937 A    3/1995   Nikolaides et al.
5,446,153 A    8/1995   Lindstrom et al.
5,494,916 A    2/1996   Lindstrom et al.
5,571,819 A   11/1996   Sabb et al.
5,741,908 A    4/1998   Gerster et al.
5,962,479 A   10/1999   Chen
6,525,064 B1 * 2/2003   Dellaria et al. ............. 514/303
6,545,016 B1 * 4/2003   Dellaria et al. ............. 514/303
6,545,017 B1 * 4/2003   Dellaria et al. ............. 514/303

FOREIGN PATENT DOCUMENTS

EP    0 778 277    6/1997
EP    1 082 960    3/2001
EP    1 097 709    5/2001
JP    11-80156     3/1999

* cited by examiner

Primary Examiner—D. Margaret Seaman
(74) Attorney, Agent, or Firm—Dean A. Ersfeld

(57) ABSTRACT

A process and intermediates for preparing 1H-imidazo[4,5-c]pyridin-4-amines are disclosed. The process includes providing a 4-phenoxy-1H-imidazo[4,5-c]pyridine and aminating the 4-phenoxy-1H-imidazo[4,5-c]pyridine to provide a 1H-imidazo[4,5-c]pyridin-4-amine.

39 Claims, No Drawings

PROCESS FOR IMIDAZO[4,5-C]PYRIDIN-4-AMINES

CROSS REFERENCE TO RELATED APPLICATION

This application claims the benefit of U.S. Provisional Patent Application No. 60/384,558, filed May 29, 2002.

FIELD OF THE INVENTION

This invention relates to processes for preparing 1H-imidazo[4,5-c]pyridin-4-amines and to intermediates for use in preparing 1H-imidazo[4,5-c]pyridin-4-amines.

BACKGROUND OF THE INVENTION

Certain antiviral immunomodulator 1H-imidazo[4,5-c]pyridin-4-amines and methods for their preparation are known and disclosed. For example, U.S. Pat. No. 5,494,916 (Lindstrom et al.), incorporated herein by reference, discloses a method involving the steps of forming a 1H-imidazo[4,5-c]pyridine substituted at the 4 position with a hydrogenolyzable amine and hydrogenolyzing using known catalytic hydrogenation conditions to provide the 4-amino compound.

Methods of making certain 1H-imidazo[4,5-c]quinolin-4-amines are also known. For example U.S. Pat. Nos. 4,689,338 and 4,929,624 (Gerster) disclose a method involving the step of heating the corresponding 4-chloro compound in the presence of ammonium hydroxide or ammonia under pressure to provide the 4-amino compound. U.S. Pat. No. 4,988,815 (Andre et al.) discloses a process involving amination of the 4-position of a 3-nitro-2,4-dichloroquinoline. This process too involves as a final step the reaction of animonia with 4-chloro-1H-imidazo[4,5-c]quinoline. U.S. Pat. No. 5,175,296 (Gerster) discloses a process involving the reaction of a 1H-imidazo[4,5-c]quinoline 5N-oxide with an organic isocyanate and hydrolyzing the product to provide the 4-amino compound. U.S. Pat. No. 5,367,076 (Gerster) discloses a process involving the reaction of a 1H-imidazo[4,5-c]quinoline 5N-oxide with an acylating agent and reacting the product with an aminating agent to provide the 4-amino compound. U.S. Pat. No. 5,395,937 (Nikolaides) discloses a process involving amination of the 4-position of a 3-nitroquinolin-2,4-disulfonate with a substituted amine. The final step of the process involves hydrogenolysis to provide the 4-amino compound. U.S. Pat. No. 5,741,908 (Gerster et al.) discloses a process involving the reaction of a 6H-imidazo[4,5-c]tetrazolo[1,5-a] quinoline with triphenylphosphine to provide an N-triphenylphosphinyl-1H-imidazo[4,5-c]quinolin-4-amine and a subsequent hydrolysis to provide a 1H-imidazo[4,5-c]quinoline-4-amine.

Methods of making certain 1-(substituted aryl)alkyl-1H-imidazo[4,5-c]quinolin-4-amines, 6,7,8,9-tetrahydro-1H-imidazo[4,5-c]quinolin-4-amines, 1,6,7,8-tetrahydrocyclopenta[b]imidazo[4,5-d]pyridin-4-amines, and 1,6,7,8,9,10-hexahydrocyclohepta[b]imidazo[4,5-d]pyridin-4-amines are also known. Japanese Unexamined Patent Publication No. 11-80156 discloses a process involving the reaction of the corresponding 4-chloro compound and phenol with an alkali to form the corresponding 4-phenoxy compound, which is reacted with ammonium acetate to provide the 4-amino compound.

Despite these developments in methods for making certain imidazoquinolin- and imidazopyridin-4-amines, there is a continuing need for useful, alternative processes and intermediates for preparing imidazo[4,5-c]pyridin4-amines.

SUMMARY OF THE INVENTION

This invention provides a process (I) for preparing a 1H-imidazo[4,5-c]pyridin-4-amine compound of Formula I

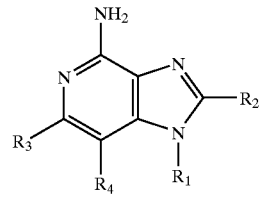

or a pharmaceutically acceptable salt thereof wherein
$R_1$ is selected from hydrogen; $CHR_xR_y$ wherein $R_x$ is hydrogen and $R_y$ is selected from alkyl or cyclic alkyl containing one to ten carbon atoms, straight chain or branched chain alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and —C=$CR_zR_z$ wherein each $R_z$ is independently alkyl or cyclic alkyl of one to six carbon atoms;
$R_2$ is selected from hydrogen; alkyl containing one to eight carbon atoms; hydroxyalkyl containing one to six carbon atoms; alkoxyalkyl wherein the alkoxy moiety contains one to four carbon atoms and the alkyl moiety contains one to six carbon atoms; benzyl; phenylethyl; and phenyl; the benzyl, phenylethyl, or phenyl substituent being optionally substituted on the benzene ring by a moiety selected from methyl, methoxy, and halogen; and morpholinoalkyl wherein the alkyl moiety contains one to four carbon atoms;
$R_3$ and $R_4$ are independently selected from hydrogen and alkyl of one to five carbon atoms; which process comprises the steps of:
(1) providing a compound of Formula II

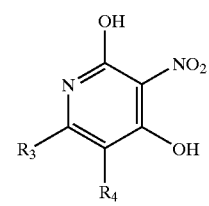

wherein $R_3$ and $R_4$ are as described above;
(2) reacting the compound of the Formula II with a chlorinating agent to provide a compound of Formula III

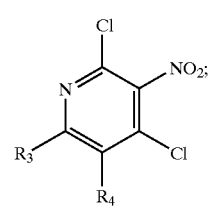

(3) reacting the compound of the Formula III with a compound of formula $R_1NH_2$, wherein $R_1$ is as defined above, to provide a compound of Formula IV

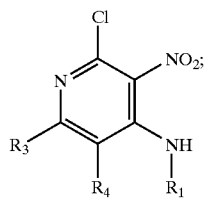

(4) reacting the compound of the Formula IV with an alkali metal phenoxide to provide a compound of Formula V

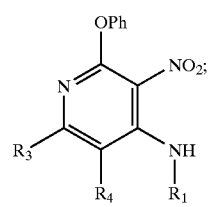

(5) reducing the compound of the Formula V to provide a compound of Formula VI

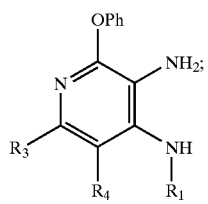

(6) reacting the compound of the Formula VI with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof, wherein $R_2$ is as defined above and each alkyl contains 1 to 8 carbon atoms, to provide a compound of Formula VIII

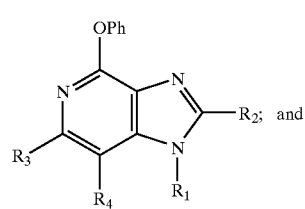

(7) reacting the compound of the Formula VIII with an aminating agent to provide the compound of the Formula I.

In some embodiments, in step (6) the compound of the Formula VI is reacted with the carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof; in the presence of cyclization conditions to provide a compound of the Formula VIII.

In some embodiments, step (6) includes the steps of:

(6a) reacting the compound of the Formula VI with a carboxylic acid of the formula $R_2CO_2H$ or the corresponding acyl halide to provide a compound of Formula VII

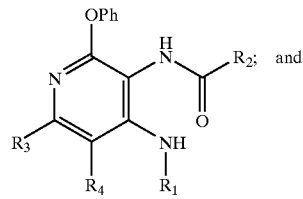

(6b) subjecting the compound of the Formula VII to cyclization conditions, during step (6a) or subsequent to the completion of step (6a), to provide a compound of the Formula VIII.

In some embodiments the above process (I) further comprises the step of isolating the compound of the Formula I or a pharmaceutically acceptable salt thereof.

In another embodiment this invention provides a process (II) for preparing a 1H-imidazo[4,5-c]pyridin-4-amine compound of the Formula I

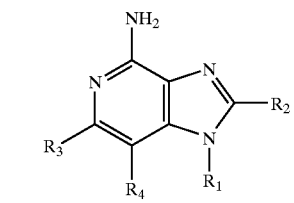

or a pharmaceutically acceptable salt thereof wherein $R_1$ is selected from hydrogen; $CHR_xR_y$ wherein $R_x$ is hydrogen and $R_y$ is selected from alkyl or cyclic alkyl containing one to ten carbon atoms, straight chain or branched chain alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and —C=$CR_zR_z$ wherein each $R_z$ is independently alkyl or cyclic alkyl of one to six carbon atoms;

$R_2$ is selected from hydrogen; alkyl containing one to eight carbon atoms; hydroxyalkyl containing one to six carbon atoms; alkoxyalkyl wherein the alkoxy moiety contains one to four carbon atoms and the alkyl moiety contains one to six carbon atoms; benzyl; phenylethyl; and phenyl; the benzyl, phenylethyl, or phenyl substituent being optionally substituted on the benzene ring by a moiety selected from methyl, methoxy, and halogen; and morpholinoalkyl wherein the alkyl moiety contains one to four carbon atoms;

$R_3$ and $R_4$ are independently selected from hydrogen and alkyl of one to five carbon atoms; which process comprises the steps of:

(1) providing a compound of Formula II

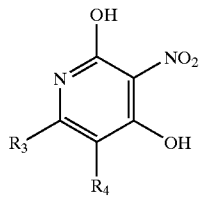

wherein $R_3$ and $R_4$ are as described above;

(2) reacting the compound of the Formula II with a chlorinating agent to provide a compound of Formula III

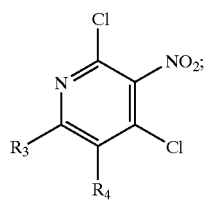

(3) reacting the compound of the Formula III with a compound of formula $R_1NH_2$, wherein $R_1$ is as defined above, to provide a compound of Formula IV

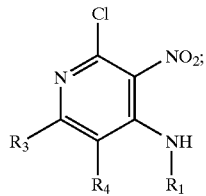

(4) reducing the compound of the Formula IV to provide a compound of Formula IX

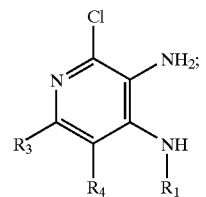

(5) reacting the compound of the Formula IX with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof, wherein $R_2$ is as defined above and each alkyl contains 1 to 8 carbon atoms to provide a compound of Formula XI

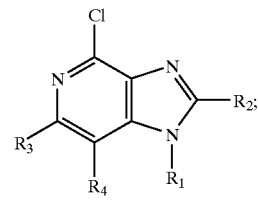

(6) reacting the compound of the Formula XI with an alkali metal phenoxide to provide a compound of Formula VIII

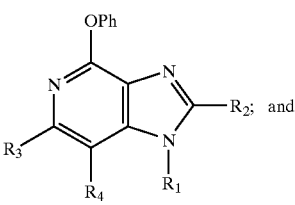

(7) reacting the compound of the Formula VIII with an aminating agent to provide a compound of the Formula I.

In some embodiments, in step (5) the compound of the Formula IX is reacted with the carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof; in the presence of cyclization conditions, to provide a compound of the Formula XI.

In some embodiments, step (5) includes the steps of:

(5a) reacting the compound of the Formula IX with a carboxylic acid of the formula $R_2CO_2H$ or the corresponding acyl halide to provide a compound of Formula X

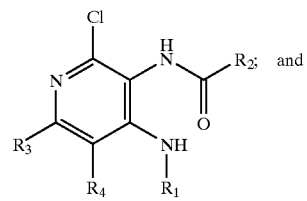

(5b) subjecting the compound of the Formula X to cyclization conditions, during step (5a) or subsequent to the completion of step (5a) to provide a compound of the Formula XI.

In some embodiments the above process (II) further comprises the step of isolating the compound of Formula I or a pharmaceutically acceptable salt thereof.

In another aspect this invention also provides compounds of the formulae

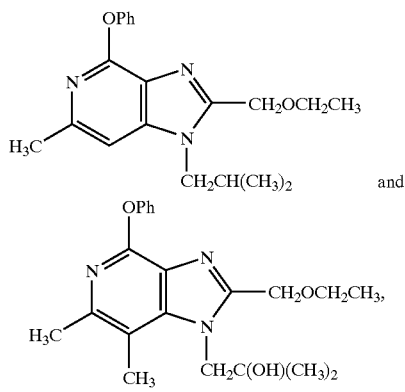

and pharmaceutically acceptable salts thereof.

DETAILED DESCRIPTION OF THE INVENTION

As used herein, "alkyl" includes straight chain alkyl and branched chain alkyl wherein the alkyl is either unsubstituted or substituted. For example, the alkyl portion of substituted alkyls such as hydroxyalkyl and alkoxyalkyl includes straight chain alkyl and branched chain alkyl.

Reaction Scheme I illustrates a process of the invention where $R_1$, $R_2$, $R_3$, and $R_4$ are as defined above, and Ph is phenyl.

In the first step of Reaction Scheme I a 2,4dihydroxy-3-nitropyridine of Formula II is provided. Many 2,4-dihydroxy-3-nitropyridines of Formula II are known and others can be readily prepared using known synthetic methods, see for example, Lindstrom et al., U.S. Pat. No. 5,446,153 and the documents cited therein. In some embodiments, $R_3$ and $R_4$ in Formula II are independently hydrogen or methyl, and in others $R_3$ and $R_4$ are both methyl.

In step (2) of Reaction Scheme I a 2,4dihydroxy-3-nitropyridine of Formula II is chlorinated using conventional chlorinating agents to provide a 2,4-dichloro-3-nitropyridine of Formula III. Examples of chlorinating agents include, but are not limited to, phosphorus oxychloride, thionyl chloride, phosgene, oxalyl chloride, and phosphorus pentachloride. In a preferred embodiment, the chlorinating agent is phosphorus oxychloride. The chlorinating agent may be used in the absence or presence of an inert solvent such as N,N-dimethylformamide or methylene chloride and at temperatures up to the reflux temperature. For example, a compound of Formula II is combined with phosphorous oxychloride and heated. The product can be isolated from the reaction mixture using conventional methods.

In step (3) of Reaction Scheme I a 2,4dichloro-3-nitropyridine of Formula III is reacted with an amine compound of formula $R_1NH_2$ to provide a 2-chloro-3-nitropyridine of Formula IV. In certain embodiments the compound of formula $R_1NH_2$ is selected from 2-hydroxy-2-methylpropylamine and 2-methylpropylamine. The reaction may be carried out in an inert solvent such as N,N-dimethylformamide or methylene chloride in the presence or in the absence of a base such as triethylamine at a temperature up to the reflux temperature of the solvent. For example, the reaction is carried out by adding the amine to a solution of a compound of Formula III in a suitable solvent such as N,N-dimethylformamide in the presence of a tertiary amine such as triethylamine. The product can be isolated from the reaction mixture using conventional methods.

In step (4) of Reaction Scheme I a 2-chloro-3-nitropyridine of Formula IV is reacted with an alkali metal phenoxide to provide a 3-nitro-2-phenoxypyridine of Formula V. For example, phenol is reacted with sodium hydride in a suitable solvent such as diglyme to form the sodium phenoxide, and the sodium phenoxide is then reacted at an elevated temperature with a compound of Formula IV. The product can be isolated from the reaction mixture using conventional methods.

In step (5) of Reaction Scheme I the compound (a 3-nitro-2-phenoxypyridine of Formula V) provided by step (4) is reduced to provide a 3-amino-2-phenoxypyridine of Formula VI. Preferably, the reduction is carried out using a conventional heterogeneous hydrogenation catalyst. The catalyst may be selected from, for example, platinum on carbon and palladium on carbon. The reaction can conveniently be carried out on a Parr apparatus in a suitable solvent such as isopropyl alcohol or toluene. Alternatively, $Ni_2B$ can be generated in situ from sodium borohydride and $NiCl_2$ in the presence of methanol. The compound of Formula V is added to the reducing agent solution to effect reduction of the nitro group. When the compound of Formula V contains an alkenylene moiety, the $Ni_2B$ reducing agent can be used without reducing the alkenylene moiety. The product can be isolated from the reaction mixture using conventional methods.

In step (6) of Reaction Scheme I a 3-amino-2-phenoxypyridine of Formula VI is reacted with a carboxylic acid of the formula $R_2CO_2H$, an equivalent thereof, or a mixture thereof, in the presence of cyclization conditions or followed by cyclization conditions to provide a 4-phenoxy-1H imidazo[4,5-c]pyridine of Formula VIII. Suitable equivalents to the carboxylic acid include compounds of the formula $R_2C(O\text{-alkyl})_3$, 1,1-dialkoxyalkyl alkanoates ($R_2C(O\text{-alkyl})_2(OOC\text{-alkyl})$), corresponding acyl halides, and mixtures thereof, wherein $R_2$ is as defined above and each alkyl contains 1 to 8 carbon atoms. The carboxylic acid or equivalent is selected such that it will provide the desired $R_2$ substituent in the compound of Formula VIII. For example, triethyl orthoformate will provide a compound where $R_2$ is hydrogen, and trimethyl orthovalerate will provide a compound where $R_2$ is butyl. In certain embodiments, $R_2$ is ethoxymethyl, and in other embodiments, $R_2$ is ethoxymethyl when $R_1$ is selected from 2-hydroxy-2-methylpropyl and 2-methylpropyl. In some embodiments, $R_2$ is ethoxymethyl when $R_1$ is selected from 2-hydroxy-2-methylpropyl and 2-methylpropyl, and $R_3$ and $R_4$ are independently hydrogen and methyl. The reaction can be run in the absence of solvent or in an inert solvent such as, for example, toluene, dichloromethane, acetonitrile, or pyridine. The product or a pharmaceutically acceptable salt thereof can be isolated from the reaction mixture using conventional methods.

The cyclization conditions include heating to an elevated temperature, such as a reflux temperature, sufficient to drive off any alcohol or water formed as a by-product of the reaction. Optionally, the presence of a catalyst such as pyridine hydrochloride can be included in the cyclization conditions. The cyclization reaction can be run in the absence of a solvent or in an inert solvent such as toluene, pyridine, or other solvent, preferably, having a boiling point of at least about 100° C.

In some embodiments, step (6) can be carried out by using steps (6a) and (6b) of Reaction Scheme I. In step (6a) a compound of the Formula VI is reacted with a carboxylic acid of the formula $R_2CO_2H$ or the corresponding acyl halide, such as $R_2C(O)Cl$ or $R_2C(O)Br$, wherein $R_2$ is as defined above, to provide an N-(4-amino-2-phenoxypyridin-3-yl)amide of Formula VII. The reaction can be run by adding the carboxylic acid, corresponding acyl halide, or mixture thereof to the compound of Formula VI dissolved in an inert solvent such as toluene, acetonitrile, pyridine or dichloromethane. The reaction can be carried out at or below ambient temperature, for example, in the range of 0 to 30° C. The product can be isolated from the reaction mixture using conventional methods.

In step (7) of Reaction Scheme I a 4-phenoxy-1H-imidazo[4,5-c]pyridine of Formula VIII is aminated to provide a 1H-imidazo[4,5-c]pyridine-4-amine of Formula I. In one embodiment, the aminating agent is ammonium acetate. The reaction can be carried out by combining a compound of Formula VIII with ammonium acetate and heating, for example, in a sealed container with heating at about 150° C. The product or a pharmaceutically acceptable salt thereof can be isolated using conventional methods.

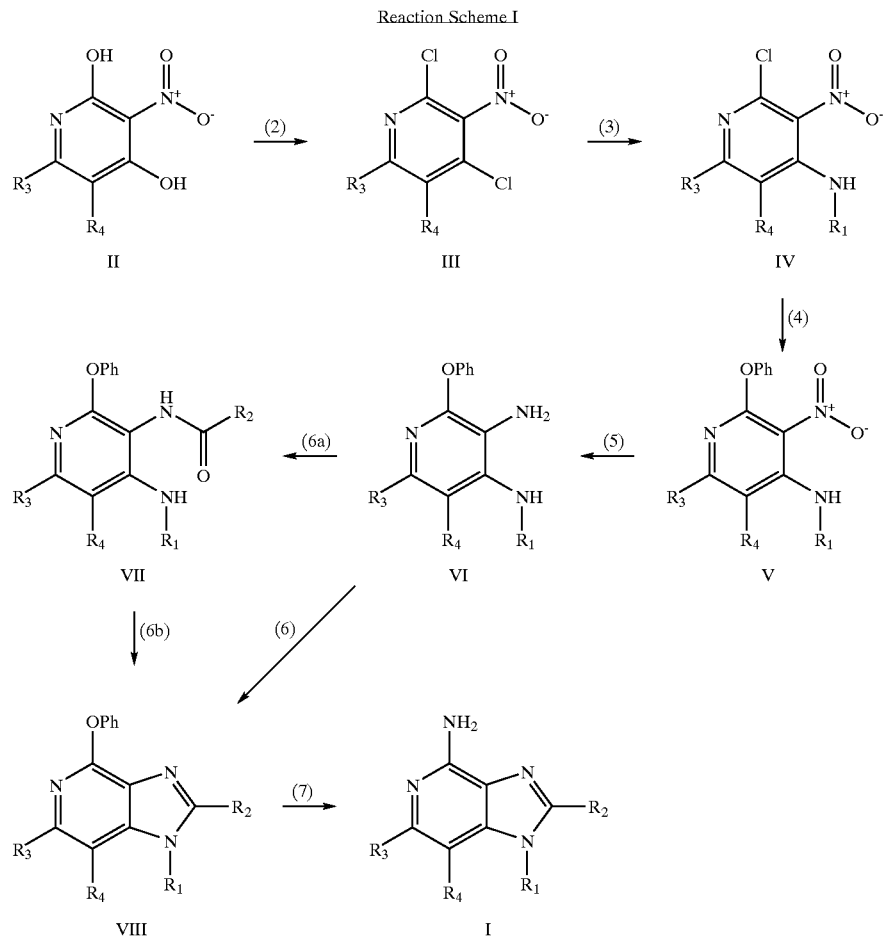

Reaction Scheme I

In step (6b) the N-(4-amino-2-phenoxypyridin-3-yl) amide of Formula VII is cyclized to provide a 4-phenoxy-1H imidazo[4,5-c]pyridine of Formula VIII. The cyclization can be carried out at an elevated temperature, such as a reflux temperature, sufficient to drive off any water formed as a by-product of the reaction. Optionally a catalyst such as pyridine hydrochloride can be included. The reaction can be run in the absence of solvent or in an inert solvent such as toluene, pyridine, or other solvents, preferably having a boiling point of at least about 100° C. Step (6b) may be run concurrently with step (6a) without first isolating the product of step (6a). The product can be isolated from the reaction mixture using conventional methods. In one embodiment, the acyl halide is ethoxyacetyl chloride, and the cyclization conditions include an elevated temperature and the presence of pyridine, preferably with pyridine hydrochloride catalyst, during the reaction of the ethoxyacetyl chloride with the compound of Formula VI.

In certain embodiments of the above process (I) $R_1$ is selected from 2-hydroxy-2-methylpropyl and 2-methylpropyl.

In certain embodiments of the above process (I) $R_2$ is ethoxymethyl.

In certain embodiments of the above process (I) $R_3$ and $R_4$ are independently hydrogen or methyl.

In other embodiments of the above process (I) $R_3$ and $R_4$ are both methyl.

In some embodiments of the above process (I) $R_1$ is selected from 2-hydroxy-2-methylpropyl and 2-methylpropyl, and $R_2$ is ethoxymethyl.

In some embodiments of the above process (I) $R_1$ is selected from 2-hydroxy-2-methylpropyl and 2-methylpropyl, $R_2$ is ethoxymethyl, and $R_3$ and $R_4$ are independently hydrogen or methyl.

In some embodiments of the above process (I), in step (6a) the carboxylic acid equivalent is the corresponding acyl halide of $R_2CO_2H$, and in step (6b) the cyclization conditions include heating to an elevated temperature and a condition selected from the presence of pyridine, and the presence of pyridine with pyridine hydrochloride.

In one embodiment of the above process (I), the acyl halide is ethoxyacetyl chloride, and the cyclization conditions include an elevated temperature and the presence of pyridine during step (6a).

In another embodiment of the above process (I), the alkali metal phenoxide is sodium phenoxide.

In another embodiment of the above process (I), the chlorinating agent is phosphorus oxychloride.

In another embodiment of the above process (I), the compound of the formula $R_1NH_2$ is selected from 2-hydroxy-2-methylpropylamine and 2-methylpropylamine.

In another embodiment of the above process (I), in step (5) the compound of Formula V is reduced with a heterogeneous hydrogenation catalyst. For example, the heterogeneous hydrogenation catalyst is selected from platinum on carbon and palladium on carbon.

In another embodiment of the above process (I), the aminating agent is ammonium acetate.

In some embodiments of the above process (I) the compound of Formula I is selected from

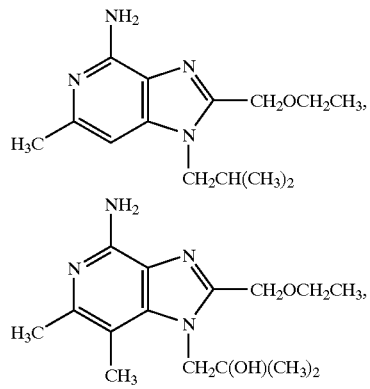

and pharmaceutically acceptable salts thereof.

Reaction Scheme II also illustrates a process of the invention where $R_1$, $R_2$, $R_3$, and $R_4$ are as defined above, and Ph is phenyl.

In the first step of Reaction Scheme II a 2,4-dihydroxy-3-nitropyridine of Formula II is provided. Many 2,4-dihydroxy-3-nitropyridines of Formula II are known and others can be readily prepared using known synthetic methods, see for example, Lindstrom et al., U.S. Pat. No. 5,446,153 and the documents cited therein. In some embodiments, $R_3$ and $R_4$ of Formula II are independently hydrogen or methyl, and in others $R_3$ and $R_4$ are both methyl.

In step (2) of Reaction Scheme II a 2,4-dihydroxy-3-nitropyridine of Formula II is chlorinated using conventional chlorinating agents to provide a 2,4-dichloro-3-nitropyridine of Formula III. Examples of chlorinating agents include, but are not limited to, phosphorus oxychloride, thionyl chloride, phosgene, oxalyl chloride, and phosphorus pentachloride. Preferably the chlorinating agent is phosphorus oxychloride. The chlorinating agent may be used in the absence or presence of an inert solvent such as N,N-dimethylformamide or dichloromethane and at temperatures up to the reflux temperature. For example, a compound of Formula II is combined with phosphorous oxychloride and heated. The product can be isolated from the reaction mixture using conventional methods.

In step (3) of Reaction Scheme II a 2,4-dichloro-3-nitropyridine of Formula III is reacted with an amine compound of formula $R_1NH_2$ to provide a 2-chloro-3-nitropyridine of Formula IV. In some embodiments, the compound of formula $R_1NH_2$ is selected from 2-hydroxy-2-methylpropylamine and 2-methylpropylamine. The reaction may be carried out in an inert solvent such as N,N-dimethylformamide or dichloromethane in the presence or in the absence of a base such as triethylamine at a temperature up to the reflux temperature of the solvent. For example, the reaction is carried out by adding the amine to a solution of a compound of Formula III in a suitable solvent such as N,N-dimethylformamide in the presence of a tertiary amine such as triethyl amine. The product can be isolated from the reaction mixture using conventional methods.

In step (4) of Reaction Scheme II the compound (a 2-chloro-3-nitropyridine of Formula IV) provided by step (3) is reduced to provide a 3-amino-2-chloropyridine of Formula IX. Preferably, the reduction is carried out using a conventional heterogeneous hydrogenation catalyst, for example, platinum on carbon. The reaction can conveniently be carried out on a Parr apparatus in a suitable solvent such as isopropyl alcohol or toluene. Alternatively, $Ni_2B$ can be generated in situ from sodium borohydride and $NiCl_2$ in the presence of methanol. The compound of Formula V is added to the reducing agent solution to effect reduction of the nitro group. When the compound of Formula V contains an alkenylene moiety, the $Ni_2B$ reducing agent can be used without reducing the alkenylene moiety. The product can be isolated from the reaction mixture using conventional methods.

In step (5) of Reaction Scheme II a 3-amino-2-chloropyridine of Formula IX is reacted with a carboxylic acid of the formula $R_2CO_2H$, an equivalent thereof, or a mixture thereof, in the presence of cyclization conditions or followed by cyclization conditions to provide a 4-chloro-1H imidazo[4,5-c]pyridine of Formula XI. Suitable equivalents to the carboxylic acid include compounds of the formula $R_2C(O-alkyl)_3$, 1,1,-dialkoxyalkyl alkanoates ($R_2C(O-alkyl)_2(OOC-alkyl)$), corresponding acyl halides, and mixtures thereof, wherein $R_2$ is as defined above and each alkyl contains 1 to 8 carbon atoms. The carboxylic acid or equivalent is selected such that it will provide the desired $R_2$ substituent in the compound of Formula XI. For example, triethyl orthoformate will provide a compound where $R_2$ is hydrogen, and trimethyl orthovalerate will provide a compound where $R_2$ is butyl. In certain embodiments, $R_2$ is ethoxymethyl, and in other embodiments, $R_2$ is ethoxymethyl when $R_1$ is selected from 2-hydroxy-2-methylpropyl and 2-methylpropyl. In some embodiments, $R_2$ is ethoxymethyl when $R_1$ is selected from 2-hydroxy-2-methylpropyl and 2-methylpropyl, and $R_3$ and $R_4$ are independently hydrogen and methyl. The reaction can be run in the absence of solvent or in an inert solvent such as, for example, toluene, dichloromethane, acetonitrile, or pyridine. The product or a pharmaceutically acceptable salt thereof can be isolated from the reaction mixture using conventional methods.

The cyclization conditions include heating to an elevated temperature, such as a reflux temperature, sufficient to drive off any alcohol or water formed as a byproduct of the reaction. Optionally, the presence of a chlorinating agent such as phosphorus oxychloride can be included in the cyclization conditions. The reaction can be run in the absence of solvent or in an inert solvent such as toluene or other solvents, preferably, have a boiling point of at least about 100° C.

In some embodiments step (5) can be carried out by using steps (5a) and (5b) of Reaction Scheme II. In step (5a) a compound of the Formula IX is reacted with a carboxylic acid of the formula $R_2CO_2H$ or the corresponding acyl halide, such as $R_2C(O)Cl$ or $R_2C(O)Br$, wherein $R_2$ is as defined above, to provide an N-(4-amino-2-chloropyridin-3-yl)amide of Formula X. The reaction can be run by adding the carboxylic acid, corresponding acyl halide, or mixture thereof to the compound of Formula IX dissolved in an inert solvent such as toluene, acetonitrile, pyridine or dichloromethane. The reaction can be carried out at or below ambient temperature, for example, in the range of 0 to 30° C. Optionally, a tertiary amine, for example triethylamine, is included. The product can be isolated from the reaction mixture using conventional methods.

In step (5b) the N-(4-amino-2-chloropyridin-3-yl)amide of Formula X is cyclized to provide a 4-chloro-1H imidazo [4,5-c]pyridine of Formula XI. The cyclization can be carried out at an elevated temperature, such as a reflux temperature or about 100° C. to about 150° C., for example about 110° C. to about 135° C., sufficient to drive off any water formed as a by-product of the reaction. The reaction may be carried out in an inert solvent such as toluene, optionally in the presence of phosphorus oxychloride. Step (5b) may be run concurrently with step (5a) without first isolating the product of step (5a). The product can be isolated from the reaction mixture using conventional methods. In one embodiment, the acyl halide is ethoxyacetyl chloride, and the cyclization conditions include an elevated temperature and the presence of phosphorus oxychloride.

In step (6) of Reaction Scheme II a 4-chloro-1H imidazo [4,5-c]pyridine of Formula XI is reacted with an alkali metal phenoxide to provide a 4-phenoxy-1H-imidazo[4,5-c] pyridine of Formula VIII. For example, phenol is reacted with sodium hydride in a suitable solvent such as diglyme to form sodium phenoxide, and the sodium phenoxide is then reacted at an elevated temperature with a compound of Formula XI. The product can be isolated from the reaction mixture using conventional methods.

In step (7) of Reaction Scheme II a 4-phenoxy-1H-imidazo[4,5c]pyridine of Formula VIII is aminated to provide a 1H-imidazo[4,5-c]pyridine-4-amine of Formula I. For example, the aminating agent is ammonium acetate. The reaction can be carried out by combining a compound of Formula VIII with ammonium acetate and beating, for example, in a sealed container with heating at about 150° C. The product or a pharmaceutically acceptable salt thereof can be isolated using conventional methods.

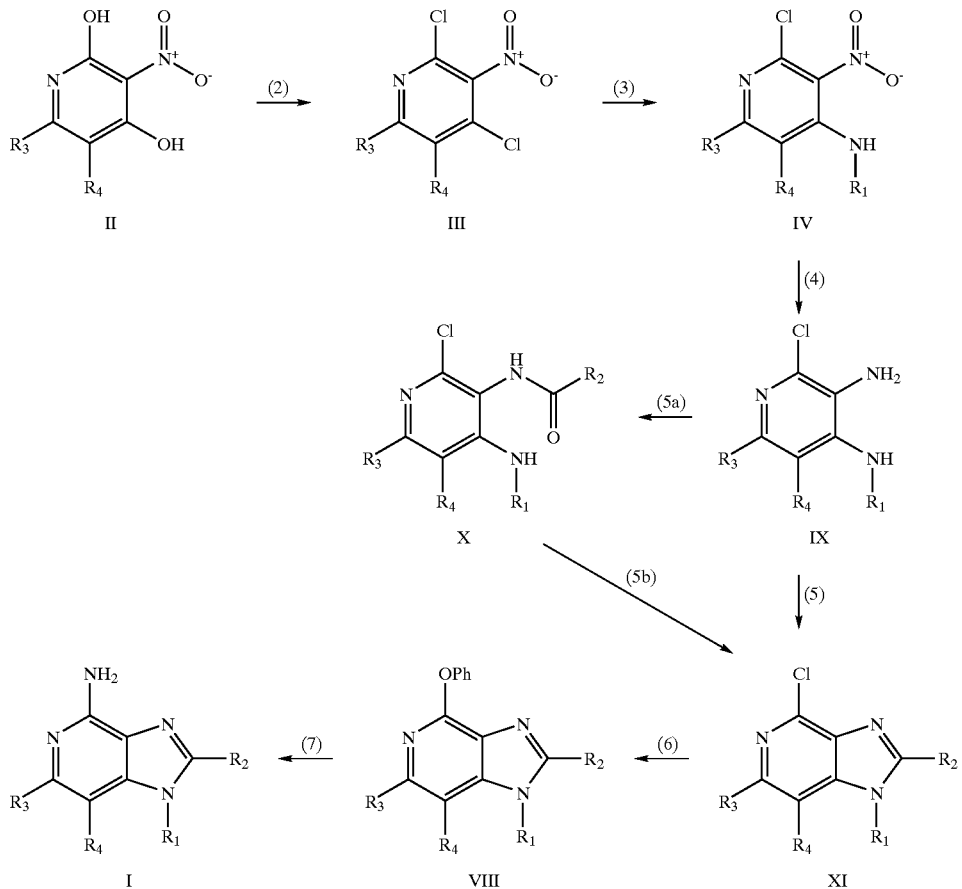

In certain embodiments of the above process (II) $R_1$ is selected from 2-hydroxy-2-methylpropyl and 2-methylpropyl.

In certain embodiments of the above process (II) $R_2$ is ethoxymethyl.

In other embodiments of the above process (II) $R_3$ and $R_4$ are independently hydrogen or methyl.

In other embodiments of the above process (II) $R_3$ and $R_4$ are both methyl.

In some embodiments of the above process (II) $R_1$ is selected from 2-hydroxy-2-methylpropyl and 2-methylpropyl, and $R_2$ is ethoxymethyl.

In some embodiments of the above process (II) $R_1$ is selected from 2-hydroxy-2-methylpropyl and 2-methylpropyl, $R_2$ is ethoxymethyl, and $R_3$ and $R_4$ are independently hydrogen or methyl.

In some embodiments of the above process (II), in step (5a) the carboxylic acid equivalent is the corresponding acyl halide of $R_2CO_2H$, and in step (5b) the cyclization conditions include an elevated temperature and the presence of phosphorus oxychloride.

In one embodiment of the above process (II), the acyl halide is ethoxyacetyl chloride, and the cyclization conditions include an elevated temperature and the presence of phosphorus oxychloride.

In another embodiment of the above process (II), the alkali metal phenoxide is sodium phenoxide.

In another embodiment of the above process (II), the chlorinating agent is phosphorus oxychloride.

In other embodiments of the above process (II), the compound of the formula $R_1NH_2$ is selected from 2-hydroxy-2-methylpropylamine and 2-methylpropylamine.

In another embodiment of the above process (II), in step (4) the compound of Formula IV is reduced with a heterogeneous hydrogenation catalyst, for example, platinum on carbon.

In another embodiment of the above process (II), the aminating agent is ammonium acetate.

In some embodiments of the above process (II) the compound of Formula I is selected from

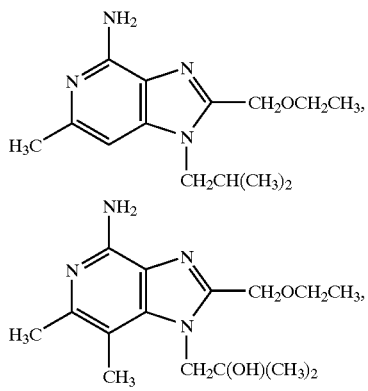

and pharmaceutically acceptable salts thereof.

The invention also provides novel compounds useful as intermediates in the synthesis of the compounds of Formula I. These compounds have the structural Formula VIII

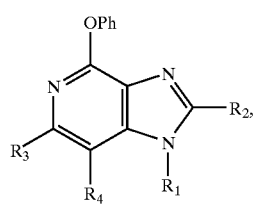

VIII wherein $R_1$, $R_2$, $R_3$, $R_4$ are as defined above, and Ph is phenyl. Examples of these include compounds of the formulae

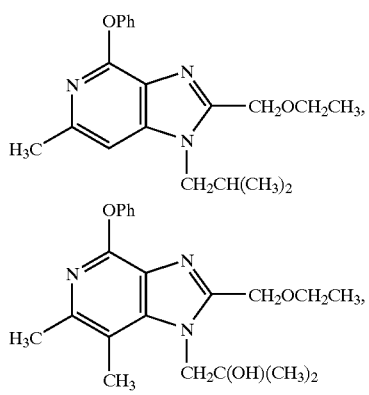

and pharmaceutically acceptable salts thereof.

The invention is further described by the following examples, which are provided for illustration only and are not intended to be limiting in any way.

EXAMPLES

Example 1

Part A

4-Hydroxy-5,6-dimethyl-2(1H)-pyridone

Ammonium hydroxide (558 ml) was added to ethyl 2-methylacetoacetate (111.66 g), and the mixture was stirred for 23 h. The resulting mixture was filtered using vacuum filtration, and the resulting crystals were washed twice with small portions of distilled water. The crystals were dried overnight in a desiccator under vacuum, yielding 46.134 g product. The filtrate was mixed with ammonium hydroxide (40 ml), and after stirring for about 3 days, the resulting supersaturated solution was cooled in an ice/salt/methanol bath with stirring. The resulting crystals were filtered, washed, and dried as above, yielding 0.9536 g ethyl 3-imino-2-methylbutanoate.

Dichloromethane (800 ml), triethylamine (50.30 ml) and 46.9716 g of the combined product from above were mixed together and cooled with an ice bath. Methyl 3-chloro-3-oxopropionate was added dropwise to the resulting solution. When addition was complete the bath was removed, and the resulting mixture was allowed to stir. After about 36 hours the resulting mixture was filtered to remove the precipitated salt. The filtrate was extracted with water (3×100 ml), dried with magnesium sulfate powder, and stored under nitrogen. The resulting dried solution was filtered, and the filtrate was concentrated under reduced pressure. Hexane (60 ml) was added to the resulting concentrate, and solvent again was removed under reduced pressure. The resulting amber solution was passed through a 3.8 cm diameter, 2.5 cm plug of silica using 30:70 ethyl acetate/hexane (2×250 ml) as the eluant. Solvent was stripped under reduced pressure from the resulting solution, and the resulting oil was dissolved in 70/30 hexane/ethyl acetate (150 ml) and passed through a second column (3.8 cm diameter, 13–15 cm plug of silica) using 70/30 hexanelethyl acetate (750 ml) as the eluant. The solvent was removed from the resulting solution under reduced pressure. The resulting product was put under high vacuum for 1 hour, yielding 77.218 g of ethyl (3E)-3-[(3-methoxy-3-oxopropanoyl)imino]-2-methylbutanoate, and stored under nitrogen.

The above amide product (77.218 g) in tetrahydrofuran (THF) (250 ml) was added dropwise to a mechanically stirred sodium hydride (NaH) solution, prepared by washing NaH (60% dispersion in oil) (25.601 g) with hexane (200 ml) and THF (100 ml) and then adding 575 ml of THF to the washed NaH. When addition was complete the reaction mixture was divided into two portions. Each portion was refluxed in a water bath for 3 hours when the reaction was quenched by addition of methanol (150 ml) to each resulting reaction mixture portion. The solvent was removed under reduced pressure from one portion, and the resulting solid (25.541 g of tan/brown powder) was combined with HCl (37%) (250 ml) and brought to reflux for 7 hours. The resulting dark solution was brought to a pH of about 7–8 with ammonia, and the resulting crystalline powder was filtered off and washed with water, resulting in 5.708 g of light tan powder, which was used in the next step.

The solvent was removed under reduced pressure from the other portion, and the resulting solid (88.4 g) was combined with HCl (37%) (880 ml) and brought to reflux for 11 hours. The resulting reaction mixture was cooled to room temperature, brought to a pH of about 7–8 with ammonium hydroxide, cooled in an ice bath, and vacuum filtered. The resulting solid was stored in a vacuum desiccator for later use in the next step.

Part B
2,4-Dihydroxy-5,6-dimethyl-3-nitropyridine

Nitric acid (65–71%) (2.95 ml) was added dropwise to a mixture of 4-hydroxy-5,6-dimethyl-2(1H)-pyridone (5.698 g) and acetic acid (about 100 ml) at about 100° C. The resulting solution was refluxed for 30 minutes and then cooled to room temperature. The resulting mixture was filtered, the resulting crystals allowed to air dry, and the solvent removed from the filtrate under reduced pressure. Water (60 ml) was added to the concentrated filtrate, and the resulting crystals were filtered and dried in a vacuum desiccator.

The above nitration process was essentially repeated using 23.612 g 4-hydroxy-5,6-dimethyl-2(1H)-pyridone, 460 ml acetic acid, 12.2 ml nitric acid, and cooling the mixture in an ice bath after refluxing and prior to filtration. Combined product was used in the next step.

Part C
2,4-Dichloro-5,6-dimethyl-3-nitropyridine 2,4-Dihydroxy-5,6-dimethyl-3-nitropyridine from Part B (31.081 g) was combined with phosphorus oxychloride (310 ml) and brought to reflux for 1.5 hour. The resulting mixture was slowly cooled to room temperature with protection from moisture and then concentrated to a solid under reduced pressure. The solid was extracted with ethyl acetate (200 ml, 2×100 ml). The combined extracts were dried with magnesium sulfate and concentrated under reduced pressure. The resulting crude product was passed through a 3.8 cm diameter by 5 cm plug of silica gel, and the resulting purified crystals (16.080 g) were used in the next step.

Part D
1-[(2-Chloro-5,6-dimethyl-3-nitropyridin4-yl)amino]-2-methylpropan-2-ol

Triethylamine (15.20 ml) was added to a solution of 2,4-dichloro-5,6-dimethyl-3-nitropyridine (16.080 g) in dimethylformamide (160 ml), and then 2-hydroxy-2-methylpropylamine (7.143 g) was added with stirring. After 1 day the resulting mixture was cooled to about 5° C. After 4 days the solvent was removed under reduced pressure, and the resulting oil was dissolved in ethyl acetate (200 ml). The resulting solution was extracted with water (3×65 ml), and the combined aqueous layers were extracted with ethyl acetate (50 ml). The combined organic layers were dried with magnesium sulfate, and the solvent was removed under reduced pressure. The crystals that formed upon cooling were recrystallized from 1:1 hexane/ethyl acetate and then from ethyl acetate. The resulting purified crystals were used in the next step.

Part E
1-[(2,3-Dimethyl-5-nitro-6-phenoxypyridin-4-yl)amino]-2-methylpropan-2-ol A solution of sodium phenoxide was prepared by washing NaH (60% in oil) (0.412 g) with hexane (20 ml), adding diglyme (5 ml) to the washed NaH, slowly adding phenol (0.911 g) in diglyme (15 ml) to the NaH, and stirring the resulting mixture for 30 minutes. 1-[(2-Chloro-5,6-dimethyl-3-nitropyridin-4-yl)amino]-2-methylpropan-2-ol (2.406 g) dissolved in 20 ml diglyme was slowly added to the phenoxide solution. After addition was complete, the resulting mixture was refluxed for 4 hours and cooled to room temperature. The solvent was removed under reduced pressure. The resulting residue was dissolved in ethyl acetate, and the ethyl acetate solution was extracted with IN potassium hydroxide (30 ml). The solvent was removed from the organic layer under reduced pressure, and the resulting product pushed through a plug of silica using 3:1 hexanelethyl acetate as the eluant.

The above was essentially repeated as follows: A solution of sodium phenoxide was prepared by washing NaH (60% in oil) (1.654 g) with hexane (75 ml), adding diglyme (20 ml) to the washed NaH, adding phenol (3.882 g) in diglyme (50 ml) to the NaH, and stirring the resulting mixture for 30 minutes. 2-Chloro-4-[(2-hydroxy-2-methylpropyl)amino]-5,6-dimethyl-3-nitropyridine (9.609 g) dissolved in 80 ml diglyme was slowly added dropwise to the phenoxide solution. After addition was complete, the resulting mixture was refluxed overnight and then cooled. The solvent was removed under reduced pressure. The resulting residue was dissolved in ethyl acetate (200 ml), and the ethyl acetate solution was extracted with 1N potassium hydroxide (KOH) (30 ml). The resulting organic layer was combined with the product of the above preparation, and the solvent was removed from the combined solution under reduced pressure. The resulting product was run through a silica column using 5:1 hexane/ethyl acetate as the eluant, and the solvent was removed under reduced pressure from the resulting solution to provide 7.213 g of product used in the next step.

Part F
1-[(3-Amino-5,6-dimethyl-2-phenoxypyridin-4-yl)amino]-2-methylpropan-2-ol To a 500 ml Parr hydrogenation flask was added 5% platinum on carbon (1.432 g) and a solution of 1-[(2,3-dimethyl-5-nitro-6-phenoxypyridin-4-yl)amino]-2-methylpropan-2-ol in 90/10 toluene/isopropanol (105 ml). The flask was evacuated until the solvent bubbled, and hydrogen was pressured into the flask at 207 kPa. After three evacuation cycles the flask was pressurized with hydrogen to 345 kPa and mixed on a shaker for about 2 hours. The pressure was released, and thin layer chromatography (TLC) monitoring of the reaction mixture indicated complete reaction. The reaction mixture was filtered, and the solvent was removed under reduced pressure. The resulting product was used in the next step.

Part G
1-[2-(Ethoxymethyl)-6,7-dimethyl-4-phenoxy-1H-imidazo[4,5-c]pyridin-1-yl]-2-methylpropan-2-ol To the product from Part F (1-[(3-amino-5,6-dimethyl-2-phenoxypyridin-4-ylamino]-2-methylpropan-2-ol was added 10 ml of pyridine. Ethoxyacetyl chloride (3.014 g) was added dropwise to the resulting mixture. The resulting solution was brought to reflux for about 3 days with an intervening day of cooling at about 5° C. The solvent was removed under reduced pressure, and the resulting product dissolved in ethyl acetate containing sodium bicarbonate. The resulting mixture was extracted with water. The resulting organic layer was dried with magnesium sulfate, the solvent was removed under reduced pressure, and the product was cooled to about 5° C. The resulting solid was recrystallized from ethyl acetate. The supernatant was concentrated under reduced pressure to the point of crystallization. This was repeated, resulting in a total of three fractions of crystals in the amounts of 1.500 g, 2.370 g, and 1.527 g, respectively.

Part H
1-[4-Amino-2-(ethoxymethyl)-6,7-dimethyl-1H-imidazo[4,5-c]pyridin-1-yl]-2-methylpropan-2-ol The three product fractions from Part G (1-[2-(ethoxymethyl)-6,7-dimethyl-4-phenoxy-1H-imidazo[4,5-c]pyridin-1-yl]-2-methylpropan-2-ol) were divided and placed in 25×150 mm culture tubes, to each of which ammonium acetate was added as shown in the following table.

| Fraction | Culture Tube Number | Product Placed in Culture Tube (g) | $NH_4OAc$ (g) |
|---|---|---|---|
| 1 | 1 | 1.464 | 15.136 |
| 2 | 2 | 1.007 | 13.327 |
| 2 | 3 | 1.333 | 10.050 |
| 3 | 4 | 0.981 | 10.269 |
| 3 | 5 | 0.465 | 5.326 |
| 1, 2, and 3 Container Rinse | 6 | 0.144 | 1.536 |

The tubes were heated in an oil bath at 150° C. for about 36 hours. After cooling to room temperature, to each tube was added 6 ml saturated sodium carbonate solution, and sufficient water to clarify. Each tube was extracted with dichloromethane (4×10 ml). All extracts were combined and extracted with 5% KOH. The KOH extracts were extracted with dichloromethane (2×25 ml). The organic layers were combined and concentrated under reduced pressure. The resulting product was subjected to column chromatography with elution solvents as follows: dichloromethane, 40:1, 20:1, 10:1, 5:1, 2:1 dichloromethane/methanol, and methanol. After cooling the resulting fractions below 0° C. for about 1 day, the fractions were combined, concentrated under reduced pressure, dissolved in a minimum amount of methanol, and treated with 1 N HCl in diethyl ether. The resulting precipitate was centrifuged, the liquid decanted off, the solid re-suspended in 50:50 methanol/diethyl ether, and re-centrifuged twice, pouring off the remaining liquid each time. After storage at below 0° C., the resulting product was dissolved in deionized water, and passed through a C-18 cartridge (Waters, SepPak, 1 g), which was then rinsed with 2:1 water/methanol containing 1% acetic acid (50 ml). The resulting solution was concentrated under reduced pressure, precipitated with saturated sodium carbonate solution, centrifuged, washed and re-centrifuged, dissolved in dichloromethane (400 ml), extracted w 10% aqueous sodium hydroxide (100 ml), concentrated under reduced pressure, and stored in a vacuum desiccator, to provide a loose powder (2.627 g), m.p. 190.5–192.9° C.

Analysis: Calculated for $C_{15}H_{24}N_4O_2$: %C, 61.62; %H, 8.27; %N, 19.16 Found: %C, 61.39; %H, 8.31; %N 19.13

Example 2

Part A
2,4-Dichloro-6-methyl-3-nitropyridine

Phosphorus oxychloride (500 ml) and 2,4-dihydroxy-6-methyl-3-nitropyridine (50.0 g) were combined and heated at 90° C. for 16 hours. The reaction mixture was cooled and the phosphorus oxychloride was removed under reduced pressure. The resulting black oil was dissolved in diethyl ether and water (2 L) (added with care). The aqueous layer was separated, made basic with sodium carbonate, and washed with diethyl ether (5×1 L). The combined organic layers were dried with magnesium sulfate and concentrated under reduced pressure. The resulting black needles were extracted with hot heptane. The hot heptane solution was filtered, and the heptane was removed to produce light brown needles (46.71 g), which were pure by NMR analysis.

Part B
2-Chloro-N-(2-methylpropyl)-6-methyl-3-nitropyridin-4-amine 2,4Dichloro-6-methyl-3-nitropyridine (39.5 g) from Part A and anhydrous dimethylformamide (400 ml) were combined and cooled to 0° C. Triethylamine (26.6 ml) and then 2-methylpropylamine (20.9 ml) were added to the resulting mixture with mixing. The reaction was complete after 16 hours, as determined by high pressure liquid chromatography (HPLC) and TLC monitoring. The dimethylformamide was removed from the resulting reaction mixture under reduced pressure, and the resulting dark yellow oil was dissolved in ethyl acetate (800 ml). The ethyl acetate solution was washed with water (3×400 ml), dried with magnesium sulfate, and the solvent was removed under reduced pressure. The resulting dark orange oil was dissolved in hexane (400 ml) and cooled to below 0° C. A seed crystal was added, and after 2 hours the resulting crystals were filtered and washed with cold (<0° C.) hexane. The crystals (30.49 g) were found to be pure by NMR analysis.

Part C
N-(2-Methylpropyl)-6-methyl-3-nitro-2-phenoxypyridin-4-amine

A solution of sodium phenoxide was prepared by adding phenol (11.57 g) in portions over a period of 0.5 hour to a solution of diglyme (42 ml) and sodium hydride (60% in oil) (5.20 g). After 0.5 hour, 2-chloro-N-(2-methylpropyl)-6-methyl-3-nitropyridin-4-amine (28.26 g) from Part B was added to the sodium phenoxide solution, and the resulting green mixture was heated to 60° C. to dissolve the starting material. After 15 minutes when the reaction was found by TLC and HPLC to be complete, any remaining sodium hydride was quenched by the addition of methanol (25 ml) with stirring. After stirring for 20 minutes, the methanol was removed from the resulting solution under reduced pressure, and the remaining dark green solution was poured into cold water (400 ml). The resulting mixture, containing a dark brown solid, was stirred for 1.5 hours, and the solid was filtered, washed with excess water, and allowed to dry. The solid was dissolved in ethyl acetate, and the ethyl acetate solution was dried with magnesium sulfate and concentrated to a brown oil under reduced pressure. The brown oil was placed under high vacuum for one hour and then triturated with hexane (250 ml). The resulting brownish red platelets (32.47 g) were filtered off and dried. NMR analysis indicated pure product.

Part D
$N^4$-(2-Methylpropyl)-6-methyl-2-phenoxypyridin-3,4-diamine

Toluene (150 ml), 5% platinum on carbon (1.55 g), and N-(2-methylpropyl)-6-methyl-3-nitro-2-phenoxypyridin-4-amine (31.00 g) from Part C were placed in a Parr hydrogenation flask at a hydrogen pressure of 345 kPa for 2 hours with shaking. The reaction was monitored by TLC and HPLC. More 5% platinum on carbon (5 g) was added. After 2 hours, another 4 g of 5% platinum on carbon was added and the reaction was continued overnight. The resulting reaction mixture was filtered, and the solvent was removed from the filtrate under reduced pressure. After one hour the resulting brown oil solidified. NMR analysis of the solid (26.37 g) indicated sufficient purity for carrying the product on to the next step.

Part E

2-Ethoxy-N-[(4-(2-methylpropylamino)-6-methyl-2-phenoxypyridin-3-yl)acetamide

Anhydrous dichloromethane (750 ml) and $N^4$-(2-methylpropyl)-6-methyl-2-phenoxypyridin-3,4-diamine (26.00 g) from Part D were combined with stirring under a nitrogen atmosphere, and cooled to 0° C. Triethylamine (13.4 ml) was added to the resulting mixture, followed by the slow addition over a period of 15 minutes of ethoxyacetyl chloride (11.74 g) dissolved in anhydrous dichloromethane (50 ml). After 15 minutes TLC monitoring indicated completion of the reaction, and the resulting reaction mixture was washed with water (3×500 ml). The organic layer was dried with magnesium sulfate and concentrated to a brown oil under reduced pressure. After drying under high vacuum, NMR analysis of the oil (32.92 g) indicated desired product of good purity.

Part F 2-(Ethoxymethyl)-1-(2-methylpropyl)-6-methyl-4-phenoxy-1H-imidazo[4,5-c]pyridine 2-Ethoxy-N-[(4-(2-methylpropylamino)-6-methyl-2-phenoxypyridin-3-yl)acetamide (31.50 g), pyridine HCl (10 g), and pyridine (250 ml) were combined and heated to reflux. The reaction was monitored by HPLC and TLC. After 24 hours an additional 10 g of pyridine HCl was added to the reaction mixture. After 48 hours the reaction was 50% complete, and a dean stark trap was used to remove 100 ml of pyridine (with) water. Pyridine (100 ml) and pyridine HCl (5 g) were added to the reaction mixture. After 36 hours the reaction was ⅔ complete, and additional pyridine was removed with the trap, followed by the addition of fresh replacement pyridine to the reaction mixture. After 5 days, the reaction was complete. The pyridine was removed from the reaction mixture under reduced pressure. Ethyl acetate (900 ml) was added to the resulting concentrate, and the resulting solution was washed with water (3×300 ml). The organic layer was dried with magnesium sulfate and concentrated to a dark amber oil (27.12 g) under reduced pressure. This oil was used in the next step.

Part G 2-(Ethoxymethyl)-1-(2-methylpropyl)-6-methyl-1H-imidazo[4,5-c]pyridin-4-amine Hydrochloride The oil from Part F (26.5 g) was combined with ammonium acetate (265 g) in a flask and heated to 150° C. in an oil bath. A paper towel was placed in the mouth of the flask to contain the subliming ammonium acetate without allowing excessive pressure in the flask. After 24 hours the reaction was complete by TLC and HPLC analysis. The reaction mixture was allowed to cool to room temperature, and the resulting dark brown oil was dissolved in chloroform (500 ml). The chloroform solution was washed with 10% aqueous sodium hydroxide (500 ml). The aqueous layer was washed with chloroform (500 ml), and the organic layers were combined, washed with water (350 ml), dried with magnesium sulfate, and concentrated to a brown oil (26 g) under reduce pressure. The oil was dissolved in isopropyl alcohol (80 ml) and salted with one equivalent of HCL (79.5 ml of 1M HCl in diethyl ether). A solid formed after one hour. The resulting mixture was cooled to below 0° C. for two hours, and the resulting white solid was filtered off, washed with cold isopropyl alcohol, and then with diethyl ether. The resulting white solid (15 g) was dissolved in ethanol (30 ml) with heating, and the solution was cooled to room temperature and seeded. Crystals slowly formed, and the solution was cooled to about 5° C. The resulting crystals were filtered off, washed with cold ethanol, and then with diethyl ether. The crystals were then crushed and dried overnight under vacuum at 80° C. to provide 10.01 g of 2-(ethoxymethyl)-1-(2-methylpropyl)-6-methyl-1H-imidazo[4,5-c]pyridin-4-amine hydrochloride, m.p. 181.0–183.0° C.

Analysis: Calculated for $C_{14}H_{22}N_4O$ (1.00 HCl): %C, 56.27; %H, 7.76; %N, 18.75 Found: %C, 56.37; %H, 7.85; %N, 18.82.

Example 3

Part A 2,4-Dichloro-6-methyl-3-nitropyridine

Phosphorus oxychloride (2000 ml) and 2,4-dihydroxy-6-methyl-3-nitropyridine (200.0 g) were combined in a flask equipped with a 20% sodium hydroxide scrubber and heated with mixing at 80° C. for 16 hours. HPLC monitoring indicted that the reaction was complete. The black reaction mixture was cooled to room temperature, and the phosphorus oxychloride was removed under reduced pressure. The resulting black oil was slowly poured into water (1500 ml) with stirring, while not exceeding a temperature of 60° C. After cooling overnight, the resulting aqueous mixture was washed with chloroform (5×1 L). The organic layers were combined, dried with magnesium sulfate, and concentrated under reduced pressure to a brown oil. The oil was dissolved in ethyl acetate (1L), and the resulting solution was washed with a 20% aqueous sodium carbonate solution (500 ml). A white solid formed and was filtered off. The filtrate was dried with magnesium sulfate and concentrated under reduced pressure to a brown solid. The solid was recrystallized from n-heptane (400 ml) to produce light brown crystals (175 g), which were used in the next step.

Part B

2-Chloro-N-(2-methylpropyl)-6-methyl-3-nitropyridin-4-amine

Product from Part A (2,4-Dichloro-6-methyl-3-nitropyridine) (125 g) and anhydrous dimethylformanide (625 ml) were combined in a nitrogen atmosphere with stirring and cooling to 0° C. Triethylamine (84.2 ml) was added, and then 2-methylpropylamine (66 ml) was added dropwise over a period of 1 hour to the resulting mixture. The reaction mixture was stirred overnight. The reaction was found to be complete by HPLC and TLC. The reaction mixture was filtered, and the dimethylformamide was removed under reduced pressure. The resulting yellow oil was dissolved in ethyl acetate (750 ml), and the resulting solution was washed with water (3×1 L), dried with magnesium sulfate, and concentrated under reduced pressure to a yellow oil. This yellow oil was dissolved in hexane (300 ml) with heating. The resulting solution was cooled to below 0° C. and after 10 minutes seeded with crystals. After 4 hours the resulting crystals were filtered off, washed with cold hexane (<0° C.), and dried at room temperature under vacuum. The resulting crystals (98 g) were found to be pure by NMR analysis.

The above was essentially repeated using 466 g starting material, 2.5 L anhydrous dimethylformanide, 314 ml triethylanine, and 246 ml 2-methylpropylamine to provide 375 g of crystals.

Part C

N-(2-Methylpropyl)-6-methyl-3-nitro-2-phenoxypyridin-4-amine

A solution of sodium phenoxide was prepared by adding phenol (192 g) dissolved in diglyme (250 ml) dropwise over a period of 1 hour to a cooled (5° C.) solution of diglyme (500 ml) and sodium hydride (60% in oil) (86 g) with a nitrogen sweep and mechanical stirring. Hydrogen gas was given off and the reaction exothermed to 24° C. After evolution of hydrogen subsided (0.5 hour), 2-chloro-N-(2-methylpropyl)-6-methyl-3-nitropyridin-4-amine (470 g) from Part B was added to the sodium phenoxide solution, and the resulting green mixture was heated to 60° C. for 0.5 hour. The reaction was found by TLC and HPLC to be complete and allowed to cool. The reaction mixture was then slowly poured into mechanically stirred, cold water (5L). After 2 hours, the resulting brown solid was filtered off, washed with excess water, and partially dried under high vacuum. The resulting solid was dissolved in ethyl acetate (3 L), and the solution dried with magnesium sulfate. The solvent was removed, leaving a dark brown solid, which was divided in two parts. Each part was mixed with hexane (1.5 L), and the resulting mixtures heated to reflux, filtered, cooled to room temperature, seeded with crystals, and cooled to below 0° C. overnight. The resulting light orange crystals were filtered off, washed with cold (<0° C.) hexane, and dried under vacuum at 60° C. overnight. NMR analysis of the dried crystals (538 g) indicated pure product.

Part D
$N^4$-(2-Methylpropyl)-6-methyl-2-phenoxypyridin-3,4-diamine

N-(2-Methylpropyl)-6-methyl-3-nitro-2-phenoxypyridin-4-amine (530 g) from Part C was dissolved in warm toluene (2.5 L). 5% Platinum on carbon (50 g) wetted with toluene was added to the resulting solution under a nitrogen atmosphere. The resulting mixture was placed in a hydrogenator, flushed multiple times with hydrogen, and filled to a hydrogen pressure of 345 kPa. The reaction was monitored by TLC and HPLC. The reaction mixture turned warn after 30 minutes, and was allowed to cooled to room temperature over 3 hours. The reaction was complete, and the resulting reaction mixture was filtered through a CELITE pad, washed with hot toluene (2 L). The CELITE pad was also washed with isopropyl alcohol. The solvent was removed from the filtrate under reduced pressure, and the resulting black oil was dissolved in dichloromethane. The resulting solution was washed with water (3×1 L), dried with magnesium sulfate, and concentrated under reduced pressure to a green solid (427 g). NMR analysis of the solid indicated sufficient purity for carrying the product on to the next step.

Part E
2-Ethoxy-N-[(4-(2-methylpropylamino)-6-methyl-2-phenoxypyridin-3-yl)acetamide Dichloromethane (2 L) and $N^4$-(2-methylpropyl)-6-methyl-2-phenoxypyridin-3,4-diamine (105 g) were combined with mechanical stirring under a nitrogen atmosphere, and cooled to 3° C. with an ice bath. Ethoxyacetyl chloride (47.4 g) dissolved in dichloromethane (500 ml) was added dropwise to the resulting mixture over 40 minutes. After the addition was completed the ice bath was removed. After one hour when TLC analysis of the reaction mixture indicated completion, the resulting reaction mixture was washed with water (3×1 L). The organic layer was dried with magnesium sulfate and concentrated to a black oil under reduced pressure. NMR analysis of the oil indicated desired product of good purity.

The above was repeated three times to provide a total of 541 g of product.

Part F
2-(Ethoxymethyl)-1-(2-methylpropyl)-6-methyl-4-phenoxy-1H-imidazo[4,5-c]pyridine 2-Ethoxy-N-[(4-(2-methylpropylanino)-6-methyl-2-phenoxypyridin-3-yl)acetamide (525 g), pyridine HCl (250 g), and pyridine (3.75 L) were combined under a nitrogen atmosphere and with mechanical stirring and heated to reflux. The reaction was monitored daily for 7 days by HPLC. Each day an additional 50 g of pyridine HCl was added, 500 ml of pyridine was removed from the reaction mixture using a dean stark trap, and 500 ml of fresh pyridine was added. After 7 days, the reaction was complete, and the resulting reaction mixture was cooled to room temperature. Some pyridine HCl precipitated out. This was filtered off and washed with ethyl acetate. The combined filtrate and ethyl acetate wash was concentrated to a black oil under reduced pressure. The oil was dissolved in ethyl acetate (4 L), and the resulting solution was divided into equal parts, each of which was washed with water (3×1 L). The combined organic layers were dried with magnesium sulfate and concentrated to a black oil under reduced pressure. This oil was dried under high vacuum to provide 460 g of product. NMR analysis of the dried oil indicated good purity, and the oil was used in the next step.

Part G
2-(Ethoxymethyl)-1-(2-methylpropyl)-6-methyl-1H-imidazo[4,5-c]pyridin-4-amine Ethanesulfonate The oil from Part F (200 g) (2-(ethoxymethyl)-1-(2-methylpropyl)-6-methyl-4-phenoxy-1H-imidazo[4,5-c]pyridine) was combined with ammonium acetate (2 kg) in a flask equipped with a mechanical stirrer and Claisen adaptor and heated to 140° C. A paper towel was placed in the open neck of the flask and one neck of the Claisen adaptor to allow the gases to escape while retaining most of the ammonium acetate. After mixing overnight the reaction was complete as determined by HPLC analysis. The reaction mixture was allowed to cool to room temperature, and was then slowly poured into a 25% aqueous sodium hydroxide solution. The resulting mixture (pH 13–14) was allowed to cool and was split into two portions. Each portion was washed with chloroform (2×1 L). The chloroform layers were combined, dried with magnesium sulfate, and concentrated under reduced pressure to a black oil, which solidified. The black oil was dissolved in chloroform (2 L), and the resulting solution was washed with water (1 L), dried with magnesium sulfate, and concentrated to a black oil.

The above process was repeated using 201 g of 2-(ethoxymethyl)-1-(2-methylpropyl)-6-methyl-4-phenoxy-1H-imidazo[4,5-c]pyridine. The resulting black oil was combined with the above black oil to give 322 g, which by NMR analysis was approximately 90% pure. The oil was dissolved in isopropyl alcohol (1.3 L) with heat. To the resulting solution cooled to 15° C. was slowly added 1067 ml 1M HCl in diethyl ether with mechanical stirring over a one hour period. The resulting reaction mixture maintained a constant temperature with cooling with an ice bath. A white solid formed, and after the addition was complete the ice bath was removed and stirring was continued for one hour. The resulting mixture was filtered, and the solid was washed with isopropyl alcohol (2 L) and diethyl ether (1 L). The resulting white solid was dried overnight under vacuum at 80° C. to provide 268 g of the HCl salt. The HCl salt was split into two portions, and each portion was heated to reflux in isopropyl alcohol (1.2 L). After the HCl salt dissolved, the solutions were cooled, causing white crystals to form. After cooling for 2 hours at about 5° C., the solid was filtered off and washed with cold isopropyl alcohol (2 L). The white solid was dried under vacuum at 80° C. to give 238 g of HCl salt, that was pure by NMR analysis.

The HCl salt was dissolved in water (2.3 L) with mechanical stirring. Sodium carbonate (230 g) was added to the resulting solution, causing a light brown oil to separate from the water. After 2 hours chloroform (1 L) was added to the mixture, and the organic layer was separated, washed with water (1 L), dried with sodium sulfate, and concentrated under reduced pressure to a light brown oil (212 g).

The oil was dissolved in isopropyl alcohol (800 ml) with heat. To the resulting mechanically stirred solution was added 95% ethansulfonic acid (65 ml) slowly over a 20 minute period. The temperature of the reaction mixture increased from 30° C. to 49° C. when the addition was complete. A white solid separated out and the resulting reaction mixture was cooled by ice bath with continued mixing for I hour. The white solid was filtered off, washed with cold isopropyl alcohol (2 L) and diethyl ether (1 L), and dried overnight under vacuum at 80° C., to provide 268 g of 2-(ethoxymethyl)-1-(2-methylpropyl)-6-methyl-1H-imidazo[4,5-c]pyridin-4-amine ethanesulfonate, m.p. 183.0–185.0° C.

Analysis: Calculated for $C_{14}H_{22}N_4O$ (1.00 $C_2H_6SO_3$): %C, 51.59; %H, 7.58; %N, 15.04 Found: %C, 51.59; %H, 7.51; %N, 14.99.

Example 4

Part A
2-Chloro-N-(2-methylpropyl)-6-methyl-3-nitropyridin4-amine 2,4-Dichloro-6-methyl-3-nitropyridine (28.75 g) and anhydrous dimethylformamide (300 ml) were combined and cooled to 0° C. Triethylamine (19.4 ml) and then 2-methylpropylamine (13.8 ml) were added to the resulting mixture. The reaction was not complete as determined by HPLC and TLC after 16 hours. An additional 1.38 ml of 2-methylpropylamino was added to the reaction mixture, and after another hour the reaction was complete. The dimethylformamide was removed from the resulting reaction mixture under reduced pressure, and the resulting dark yellow oil was dissolved in ethyl acetate. The ethyl acetate solution was washed with water (3×), dried with magnesium sulfate, and the solvent was removed under reduced pressure. The resulting yellow oil was dissolved in hexane and cooled to below 0° C. overnight. A yellow solid formed. The yellow solid was washed with cold (<0° C.) hexane and filtered. The remaining crystals (22.02 g) were found to be pure by NMR analysis and used in the next step.

Part B
2-Chloro-$N^4$-2-methylpropyl)-6-methylpyridin-3,4-diamine

2-Chloro-N-(2-methylpropyl)-6-methyl-3-nitropyridin-4-amine (21.95 g) from Part A, toluene (200 ml), and 5% Platinum on carbon (2.20 g) were placed in a hydrogenator at a hydrogen pressure of 345 kPa for 2 hours. The reaction, monitored by HPLC, was complete, and the resulting reaction mixture was filtered through a fluted filter paper and then through a folded No. 2 Whatman filter. The solvent was removed from the filtrate under reduced pressure, and the resulting brown oil solidified after one hour. NMR analysis of the solid indicated sufficient purity for carrying the product (19.03 g) on to the next step.

Part C
N-[2-Chloro-4-(2-methylpropylamino)-6-methylpyridin-3-yl]-2-ethoxyacetamide Anhydrous dichloromethane (750 ml) and 2-chloro-N4-(2-methylpropyl)-6-methylpyridin-3,4-diamine (18.84 g) were combined and cooled to 0° C. Triethylamine (12.9 ml) was added dropwise to the resulting mixture, and then ethoxyacetyl chloride (11.34 g) dissolved in anhydrous dichloromethane (50 ml) was added slowly to the resulting mixture, which turned dark. After two hours the dark mixture was allowed to warm to room temperature. TLC analysis of the reaction mixture indicated completion, and the solvent was removed under reduced pressure. The resulting yellow solid was dissolved in chloroform, and the resulting solution was washed with water. The organic layer was dried with magnesium sulfate and concentrated to a dark brown oil (27.75 g) under reduced pressure. NMR analysis of the oil indicated desired product of suitable purity for use in the next step.

Part D
4-Chloro-2-(ethoxymethyl)-1-(2-methylpropyl)-6-methyl-1H-imidazo[4,5-c]pyridine N-(2-Chloro-4-(2-methylpropylamino)-6-methylpyridin-3-yl]-2-ethoxyacetamide (26.43 g), anhydrous toluene (400 ml), and phosphorus oxychloride (74 ml) were combined and heated to 110° C. for 16 hours. HPLC analysis of the resulting reaction mixture indicated 30% completion. The reaction mixture was heated to reflux for an additional 24 hours when the reaction was found to be complete. The resulting reaction mixture was cooled, and the phosphorus oxychloride and toluene were removed under reduced pressure. The resulting black oil was dissolved in ethyl acetate and water, and the aqueous layer was made basic with sodium carbonate. The basic aqueous layer was washed with ethyl acetate (2×). The organic layers were combined, dried with magnesium sulfate, and concentrated to a black oil under reduced pressure. The oil was extracted with hot hexane. The resulting hexane solution was filtered hot, and the filtrate was cooled to below 0° C. overnight The resulting orange and black crystals were washed with cold hexane. NMR analysis of the resulting product (14.02 g) indicated only minor impurities, and the product was carried on to the next step.

Part E
2-(Ethoxymethyl)-1-(2-methylpropyl)-6-methyl-4-phenoxy-1H-imidazo[4,5-c]pyridine To a chilled solution of diglyme (3 ml) and sodium hydride (60% in oil) (0.075 g) was added phenol (0.17 g) in portions. Hydrogen was given off and the reaction was continued 0.5 hour until the bubbling stopped. 4-Chloro-2-(ethoxymethyl)- 1-(2-methylpropyl)-6-methyl-1H-imidazo [4,5-c]pyridine (0.47 g) from Part D dissolved in diglyme (2 ml) was added dropwise to the resulting reaction mixture. When addition was complete the resulting dark brown reaction solution was heated to reflux. After 48 hours, HPLC analysis indicated no further reaction. The solvent was removed from the resulting reaction solution under reduced pressure, and the resulting black oil was dissolved in dichloromethane. The dichloromethane solution was washed with 5% aqueous sodium hydroxide (100 ml), and the resulting basic aqueous layer was washed with dichloromethane (2×). The organic layers were combined, dried with magnesium sulfate, and concentrated to a black oil under reduced pressure.

The above process was repeated using 50 ml diglyme, 2.15 g sodium hydride (60% in oil), 4.80 g phenol, and 13.55 g starting material. The resulting black oil was combined with that from the above process and passed through a column of silica using 20/80 ethyl acetate/hexane. After removing the solvent under reduced pressure from the eluted solution, NMR analysis of the resulting yellow oil (9.30 g) indicated pure product, which was used in the next step.

Part F
2-(Ethoxymethyl)-1-(2-methylpropyl)-6-methyl-1H-imidazo[4,5-c]pyridin-4-amine Hydrochloride A sealed glass tube containing 2-(ethoxymethyl)-1-2-methylpropyl)-6-methyl-4-phenoxy-1H-imidazo[4,5-c]pyridine (9.07 g) from Part E and ammonium acetate (80 g) was heated to 150° C. with stirring. After 2 days HPLC and TLC monitoring indicated formation of the 4-hydroxy impurity at 6% and that the reaction was complete. The resulting reaction mixture was cooled to room temperature, and the resulting dark amber oil was dissolved in chloroform (500 ml). The chloroform solution was washed with 10% aqueous sodium hydroxide (357 ml). The resulting basic aqueous layer was washed with chloroform (500 ml), and the organic layers were combined, washed with water (200 ml), dried with magnesium sulfate, and concentrated under reduced pressure to an amber oil. This was dissolved in isopropyl alcohol (50 ml) with heat. To the resulting solution cooled to room temperature was added 23.8 ml of 1N HCl in diethyl ether. A white solid formed, and after 1 hour the resulting mixture was cooled to below 0° C. for 2 hours. The resulting white solid was filtered off and washed with cold isopropyl alcohol and then with diethyl ether. The white solid was then dried under vacuum at 80° C. for 2 days to provide 6.00 g of 2-(ethoxymethyl)-1-(2-methylpropyl)-6-methyl-1H-imidazo[4,5-c]pyridin-4-amine hydrochloride, m.p. 181.0–183.0° C.

Analysis: Calculated for $C_{14}H_{22}N_4O$ (1.00 HCl): %C, 56.27; %H, 7.76; %N, 18.75 Found: %C, 56.33; %H, 7.81; %N, 18.68.

Example 5

Part A

2-Chloro-N-(2-methylpropyl)-6-methyl-3-nitropyridin-4-amine 2,4-Dichloro-6-methyl-3-nitropyridine (7.01 g), anhydrous dimethylformamide (70 ml), and triethylamine (4.72 ml) were combined and cooled to 0° C. 2-Methylpropylamine (3.36 ml) was added dropwise to the resulting mixture. The reaction was stalled at 75% completion, as determined by HPLC and TLC monitoring, after 16 hours. The dimethylformamide was removed from the resulting reaction mixture under reduced pressure, and the resulting oil was dissolved in ethyl acetate. The ethyl acetate solution was washed with water, dried with magnesium sulfate, and the solvent was removed under reduced pressure. The resulting yellow oil was put through a column of silica using 90/10 hexane/ethyl acetate. After removing the solvent from the resulting eluted solution, the resulting yellow oil (5.0 g) was dried under high vacuum and used in the next step.

Part B

2-Chloro-$N^4$-(2-methylpropyl)-6-methyl pyridin-3,4-diamine

2-Chloro-N-(2-methylpropyl)-6-methyl-3-nitropyridin-4-amine (5.00 g) from Part A, toluene (100 ml), and 5% platinum on carbon (3.5 g) were added to a Parr shaker and placed on a hydrogenator at a hydrogen pressure of 345 kPa for 4 hours. The reaction, monitored by HPLC, was complete, and the resulting reaction mixture was filtered through a fluted filter paper and then through a folded No.2 Whatman filter. The solvent was removed from the filtrate under reduced pressure, and the resulting oil (4.14 g) was carried on to the next step.

Part C

N-[2-Chloro-4-(2-methylpropylamino)-6-methylpyridin-3-yl]-2-ethoxyacetamide

Anhydrous dichloromethane (300 ml), 2-chloro-$N^4$-(2-methylpropyl)-6-methyl pyridin-3,4-diamine (4.14 g) from Part B and triethylamine (2.93 ml) were combined and cooled to 0° C. To the resulting mixture was added dropwise ethoxyacetyl chloride (2.49 g). After 1 hour the resulting reaction mixture was allowed to warm to room temperature. After 2 hours, the reaction, monitored by HPLC, was complete, and the solvent was removed under reduced pressure. The resulting yellow oil was dissolved in ethyl acetate, and the resulting solution was washed with water. The organic layer was dried with magnesium sulfate and concentrated to a yellow oil under reduced pressure. The yellow oil was put through a column of silica gel using 20/80 ethyl acetate/hexane. NMR analysis of the oil obtained after removal of the solvent under reduce pressure indicated desired product (3.64 g) of good purity for use in the next step.

Part D

4Chloro-2-(ethoxymethyl)-1-(2-methylpropyl)-6-methyl-1H-imidazo[4,5-c]pyridine

N-[2-Chloro-4-(2-methylpropylamino)-6-methylpyridin-3-yl]-2-ethoxyacetamide (3.64 g), anhydrous toluene (100 ml), and phosphorus oxychloride (10.2 ml) were combined in a sealed glass tube and heated to 135° C. for 16 hours. The resulting reaction mixture was cooled, and the phosphorus oxychloride and toluene were removed under reduced pressure. The resulting black oil was dissolved in ethyl acetate, and the resulting solution was washed with saturated aqueous sodium bicarbonate. The basic aqueous layer was then washed with ethyl acetate. The organic layers were combined and concentrated to a black oil under reduced pressure. The oil was put through a column of silica gel using 60/40 ethyl acetate/hexane. The resulting eluted solution was dried under reduced pressure to a brown oil, which solidified after sitting for 48 hours. NMR analysis of the resulting product (2.59 g) indicated only minor impurities, and the product was carried on to the next step.

Part E 2-(Ethoxymethyl)-1-(2-methylpropyl)-6-methyl-4-phenoxy-1H-imidazo[4,5-c]pyridine To a chilled solution of diglyme (2 ml) and sodium hydride (60% in oil) (0.15 g) was added phenol (0.035 g) in portions. Hydrogen was given off and the reaction was allowed to continue for 1 hour. 4-Chloro-2-(ethoxymethyl)-1-2-methylpropyl)-6-methyl-1H-imidazo[4,5-c]pyridine (0.10 g) from Part D was added to the resulting reaction mixture. The resulting dark brown solution was heated to reflux for two days, cooled to room temperature, and dissolved in ethyl acetate. The ethyl acetate solution was washed with water, and the organic layer was dried with magnesium sulfate and concentrated under reduced pressure.

The above was repeated using 20 ml diglyme, 0.40 g sodium hydride (60% in oil), 0.88 g phenol, and 2.49 g starting material. After refluxing for 5 days the reaction was 65% complete, but not progressing. The resulting reaction mixture was cooled to room temperature, and treated as described above. The material from both runs was combined and then purified by column chromatography using 20/80 ethyl acetate/hexane to give starting material (0.85 g) and product (1.72 g).

The recovered starting material (0.85 g) was reacted as described above using 5 ml diglyme, 0.14 g sodium hydride (60% in oil), and 0.30 g phenol. When the addition of starting material to the sodium phenoxide solution was complete the resulting dark brown reaction solution was heated to reflux for 24 hours. The reaction was complete as determined by HPLC, and the resulting reaction solution was cooled to room temperature and treated as described above, except that the brown oil was passed through a column using 30/70 ethyl acetate/hexane. The resulting solution was concentrated under reduced pressure to give a brown oil product (0.79 g), which was found to be pure by TLC analysis. Combined product from each of the above three preparations was used in the next step.

Part F
2-Ethoxymethyl)-1-(2-methylpropyl)-6-methyl-1H-imidazo[4,5-c]pyridin-4-amine A sealed glass tube containing 2-(ethoxymethyl)-1-(2-methylpropyl)-6-methyl-4-phenoxy-1H-imidazo[4,5-c]pyridine (2.51 g) from Part E and ammonium acetate (25.1 g) was heated to 150° C. After 36 hours, TLC monitoring indicated that the reaction was complete. The resulting reaction mixture was cooled and then dissolved in ethyl acetate. The ethyl acetate solution was washed with 25% aqueous sodium hydroxide. The resulting organic layer was dried with magnesium sulfate, and concentrated under reduced pressure to an orange oil. The oil was put through a column using 95/5 ethyl acetate/methanol, providing good separation. The oil recovered from the product fraction was dissolved in isopropyl alcohol, to which 1M HCl in diethyl ether was added. A white solid formed. More diethyl ether was added, and the white solid was filtered and dried under vacuum at 80° C. for 5 hours. The resulting solid was dissolved in water (50 ml), and the pH was adjusted to 11 using sodium carbonate. An oil separated and was extracted with dichloromethane. The resulting dichloromethane solution was dried with magnesium sulfate and concentrated under reduced pressure to a clear oil. The oil was triturated with methanol, and the resulting solid was dissolved in diethyl ether. The diethyl ether solution was subjected to high vacuum at room temperature to dry the product. The resulting partially solidified product was solidified by cooling with an isopropyl alcohol/dry ice bath to provide 2-(ethoxymethyl)-1-(2-methylpropyl)-6-methyl-1H-imidazo[4,5-c]pyridin-4-amine, m.p. 77.0–79.0° C.

Analysis: Calculated for $C_{14}H_{22}N_4O$: %C, 64.09; %H, 8.45; %N, 21.36 Found: %C, 63.84; %H, 8.32; %N, 21.08.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A process for preparing a 1H-imidazo[4,5-c]pyridin4-amine compound of Formula I

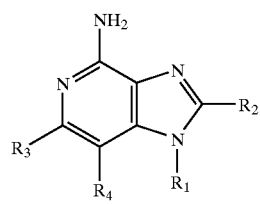

or a pharmaceutically acceptable salt thereof wherein
$R_1$ is selected from hydrogen; $CHR_xR_y$, wherein $R_x$ is hydrogen and $R_y$ is selected from alkyl or cyclic alkyl containing one to ten carbon atoms, straight chain or branched chain alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and
—C=$CR_zR_z$ wherein each $R_z$ is independently alkyl or cyclic alkyl of one to six carbon atoms;

$R_2$ is selected from hydrogen; alkyl containing one to eight carbon atoms; hydroxyalkyl containing one to six carbon atoms; alkoxyalkyl wherein the alkoxy moiety contains one to four carbon atoms and the alkyl moiety contains one to six carbon atoms; benzyl, phenylethyl; and phenyl; the benzyl, phenylethyl, or phenyl substituent being optionally substituted on the benzene ring by a moiety selected from methyl, methoxy, and halogen; and morpholinoalkyl wherein the alkyl moiety contains one to four carbon atoms;

$R_3$ and $R_4$ are independently selected from hydrogen and alkyl of one to five carbon atoms; which process comprises the steps of:

(1) providing a compound of Formula II

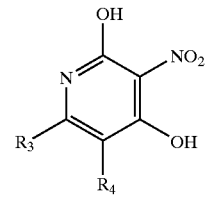

wherein $R_3$ and $R_4$ are as described above;

(2) reacting the compound of the Formula II with a chlorinating agent to provide a compound of Formula III

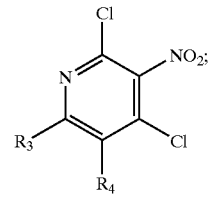

(3) reacting the compound of the Formula III with a compound of formula $R_1NH_2$, wherein $R_1$ is as defined above, to provide a compound of Formula IV

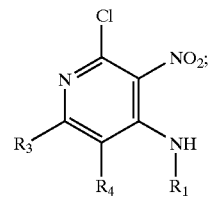

(4) reacting the compound of the Formula IV with an alkali metal phenoxide to provide a compound of Formula V

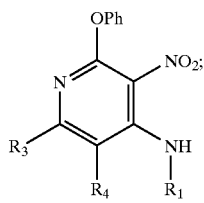

V (5) reducing the compound of the Formula V to provide a compound of Formula VI

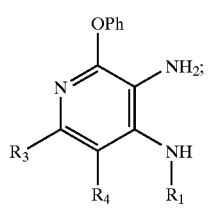

VI (6) reacting the compound of the Formula VI with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof, wherein $R_2$ is as defined above and each alkyl contains 1 to 8 carbon atoms, to provide a compound of Formula VIII

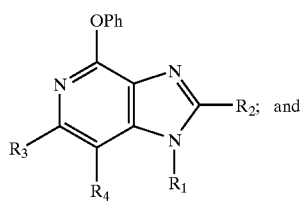

VIII (7) reacting the compound of the Formula VIII with an aminating agent to provide a compound of the Formula I.

2. The process according to claim 1, wherein in step (6) the compound of the Formula VI is reacted with the carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof; in the presence of cyclization conditions to provide a compound of the Formula VIII.

3. The process of claim 1, wherein step (6) includes the steps of:

(6a) reacting the compound of the Formula VI with a carboxylic acid of the formula $R_2CO_2H$ or the corresponding acyl halide to provide a compound of Formula VII

VII (6b) subjecting the compound of the Formula VII to cyclization conditions, during step (6a) or subsequent to the completion of step (6a), to provide a compound of the Formula VIII.

4. The process of claim 3, wherein in step (6a) the carboxylic acid equivalent is the corresponding acyl halide of $R_2CO_2H$, and in step (6b) the cyclization conditions include heating to an elevated temperature and a condition selected from the presence of pyridine, and the presence of pyridine with pyridine hydrochloride.

5. The process of claim 4, wherein the acyl halide is ethoxyacetyl chloride, and wherein the cyclization conditions include an elevated temperature and the presence of pyridine during step (6a).

6. The process of claim 1, further comprising the step of isolating the compound of Formula I or a pharmaceutically acceptable salt thereof.

7. The process of claim 1, wherein $R_1$ is selected from 2-hydroxy-2-methylpropyl and 2-methylpropyl.

8. The process of claim 1, wherein $R_2$ is ethoxymethyl.

9. The process of claim 1, wherein $R_3$ and $R_4$ are independently hydrogen or methyl.

10. The process of claim 1, wherein $R_3$ and $R_4$ are both methyl.

11. The process of claim 1, wherein $R_1$ is selected from 2-hydroxy-2-methylpropyl and 2-methylpropyl, and wherein $R_2$ is ethoxymethyl.

12. The process of claim 11, wherein $R_3$ and $R_4$ are independently hydrogen or methyl.

13. The process of claim 1, wherein the compound of Formula I is selected from

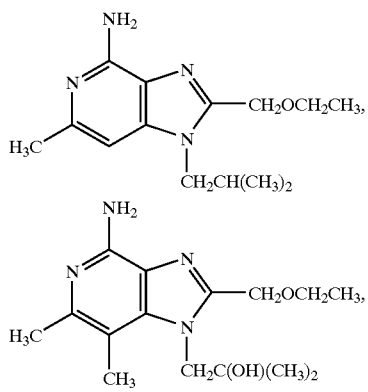

and pharmaceutically acceptable salts thereof.

14. The process of claim 1, wherein the alkali metal phenoxide is sodium phenoxide.

15. The process of claim 1, wherein the chlorinating agent is phosphorus oxychloride.

16. The process of claim 1, wherein the compound of the formula $R_1NH_2$ is selected from 2-hydroxy-2-methylpropylamine and 2-methylpropylamine.

17. The process of claim 1, wherein in step (5) the compound of Formula V is reduced with a heterogeneous hydrogenation catalyst.

18. The process of claim 17, wherein the heterogeneous hydrogenation catalyst is selected from platinum on carbon and palladium on carbon.

19. The process of claim 1, wherein the aminating agent is ammonium acetate.

20. A process for preparing a 1H-imidazo[4,5-c]pyridin-4-amine compound of Formula I

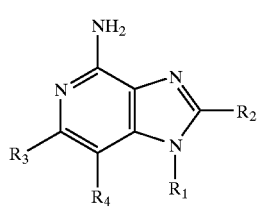

I or a pharmaceutically acceptable salt thereof wherein $R_1$ is selected from hydrogen; $CHR_xR_y$ wherein $R_x$ is hydrogen and $R_y$ is selected from alkyl or cyclic alkyl containing one to ten carbon atoms, straight chain or branched chain alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and —C=CR_zR_z wherein each $R_z$ is independently alkyl or cyclic alkyl of one to six carbon atoms;

$R_2$ is selected from hydrogen; alkyl containing one to eight carbon atoms; hydroxyalkyl containing one to six carbon atoms; alkoxyalkyl wherein the alkoxy moiety contains one to four carbon atoms and the alkyl moiety contains one to six carbon atoms; benzyl; phenylethyl; and phenyl; the benzyl, phenylethyl, or phenyl substituent being optionally substituted on the benzene ring by a moiety selected from methyl, methoxy, and halogen; and morpholinoalkyl wherein the alkyl moiety contains one to four carbon atoms;

$R_3$ and $R_4$ are independently selected from hydrogen and alkyl of one to five carbon atoms; which process comprises the steps of:

(I) providing a compound of Formula II

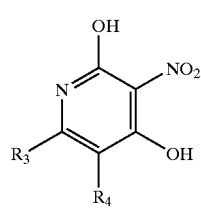

II wherein $R_3$ and $R_4$ are as described above;

(2) reacting the compound of the Formula II with a chlorinating agent to provide a compound of Formula III

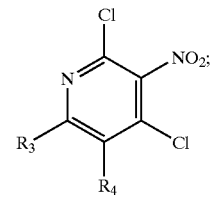

III (3) reacting the compound of the Formula III with a compound of formula $R_1NH_2$, wherein $R_1$ is as defined above, to provide a compound of Formula IV

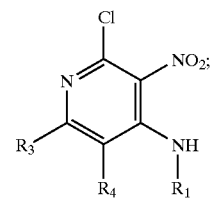

IV (4) reducing the compound of the Formula IV to provide a compound of Formula IX

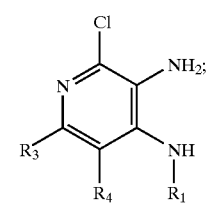

IX (5a) reacting the compound of the Formula IX with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)$C-alkyl); or a mixture thereof, wherein $R_2$ is as defined above and each alkyl contains 1 to 8 carbon atoms to provide a compound of Formula XI

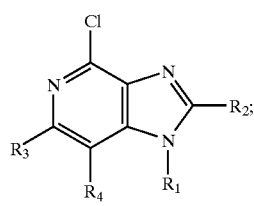

XI (6) reacting the compound of the Formula XI with an alkali metal phenoxide to provide a compound of Formula VIII

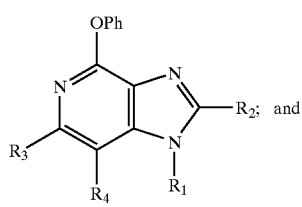

VIII (7) reacting the compound of the Formula VIII with an aminating agent to provide the compound of the Formula I.

21. The process according to claim 20, wherein in step (5) the compound of the Formula IX is reacted with the carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl}$; or a mixture thereof; in the presence of cyclization conditions, to provide a compound of the Formula XI.

22. The process according to claim 20, wherein step (5) includes the steps of:

(5a) reacting the compound of the Formula IX with a carboxylic acid of the formula $R_2CO_2H$ or the corresponding acyl halide to provide a compound of Formula X

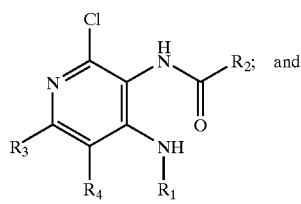

X (5b) subjecting the compound of the Formula X to cyclization conditions, during step (5a) or subsequent to the completion of step (5a) to provide a compound of the Formula XI.

23. The process of claim 20, further comprising the step of isolating the compound of Formula I or a pharmaceutically acceptable salt.

24. The process of claim 20, wherein $R_1$ is selected from 2-hydroxy-2-methylpropyl and 2-methylpropyl.

25. The process of claim 20, wherein $R_2$ is ethoxymethyl.

26. The process of claim 20, wherein $R_3$ and $R_4$ are independently hydrogen or methyl.

27. The process of claim 20, wherein $R_3$ and $R_4$ are both methyl.

28. The process of claim 20, wherein $R_1$ is selected from 2-hydroxy-2-methylpropyl and 2-methylpropyl, and wherein $R_2$ is ethoxymethyl.

29. The process of claim 28, wherein $R_3$ and $R_4$ are independently hydrogen or methyl.

30. The process of claim 20, wherein the compound of Formula I is selected from

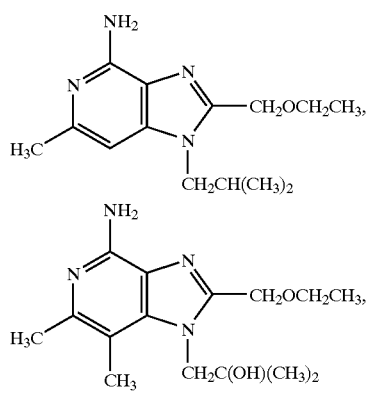

and pharmaceutically acceptable salts thereof.

31. The process of claim 20, wherein in step (5a) the carboxylic acid equivalent is the corresponding acyl halide of $R_2CO_2H$, and in step (5b) the cyclization conditions include an elevated temperature and the presence of phosphorus oxychloride.

32. The process of claim 31, wherein the acyl halide is ethoxyacetyl chloride.

33. The process of claim 20, wherein the alkali metal phenoxide is sodium phenoxide.

34. The process of claim 20, wherein the chlorinating agent is phosphorus oxychloride.

35. The process of claim 20, wherein the compound of the formula $R_1NH_2$ is selected from 2-hydroxy-2-methylpropylamine and 2-methylpropylamine.

36. The process of claim 20, wherein in step (4) the compound of Formula IV is reduced with a heterogeneous hydrogenation catalyst.

37. The process of claim 36, wherein the heterogeneous hydrogenation catalyst is platinum on carbon.

38. The process of claim 20, wherein the aminating agent is ammonium acetate.

39. A compound selected from the formulae

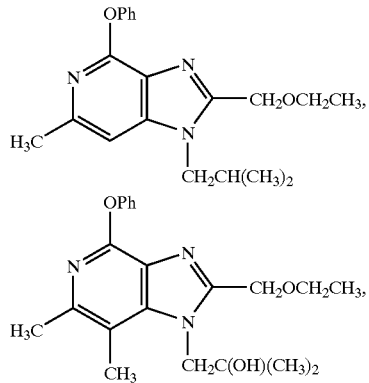

and pharmaceutically acceptable salts thereof.

* * * * *

UNITED STATES PATENT AND TRADEMARK OFFICE
CERTIFICATE OF CORRECTION

PATENT NO. : 6,743,920 B2
DATED : June 1, 2004
INVENTOR(S) : Lindstrom, Kyle J.

It is certified that error appears in the above-identified patent and that said Letters Patent is hereby corrected as shown below:

Column 1,
Line 34, delete "animonia", insert in place thereof -- ammonia --;
Line 67, delete "pyridin4-amines", insert in place thereof -- pyridine-4-amines -- ;

Column 7,
Lines 30 and 39, delete "4dihydroxy", insert in place thereof -- 4-dihydroxy --;
Line 53, delete "4dichloro", insert in place thereof -- 4-dichloro --;

Column 9,
Line 51, delete "amidc", insert in place thereof -- amide --;

Column 12,
Line 15, delete "triethyl amine", insert in place thereof -- triethylamine --;
Line 39, delete "1,-dialkoxyalkyl", insert in place thereof -- 1-dialkoxyalkyl --;

Column 14,
Line 13, delete "[4,5c], insert in place thereof -- [4,5-c] --;
Line 17, delete "beating", insert in place thereof -- heating --;

Column 16
Line 58, delete "hexanelethyl", insert in place thereof -- hexane/ethyl --;

Column 17,
Line 53, delete "nitropyridin4-yl", insert in place thereof -- nitropyridin-4-yl --;

Column 18,
Line 17, delete "IN", insert in place thereof -- 1N --;
Line 21, delete "hexanelethyl", insert in place thereof -- hexane/ethyl --;

Column 20,
Line 15, delete "4Dichloro", insert in place thereof -- 4-Dichloro --;

Column 21,
Line 63, delete "HCL", insert in place thereof -- HCl --;

Column 22,
Line 40, delete "dimethylformanide", insert in place thereof -- dimethylformamide --;
Line 61, delete "triethylanine", insert in place thereof -- triethylamine --;

UNITED STATES PATENT AND TRADEMARK OFFICE
CERTIFICATE OF CORRECTION

PATENT NO. : 6,743,920 B2
DATED : June 1, 2004
INVENTOR(S) : Lindstrom, Kyle J.

It is certified that error appears in the above-identified patent and that said Letters Patent is hereby corrected as shown below:

Column 23,
Line 1, delete "I hour", insert in place thereof -- 1 hour --;
Line 4, delete "exotherned", insert in place thereof -- exothermed --;
Line 33, delete "warn", insert in place thereof -- warm --;
Line 66, delete "2-methylpropylanino", insert in place thereof -- 2-methylpropylamino --;

Column 25,
Line 11, delete "I hour", insert in place thereof -- 1 hour --;
Line 23, delete "nitropyridin4", insert in place thereof -- nitropyridin-4 --;
Line 31, delete "2-methylpropylamino", insert in place thereof -- 2-methylpropylamine --;
Line 44, delete "$N^4$-2-methylpropyl)", insert in place thereof -- $N^4$-(2-methylpropyl) --;

Column 26,
Line 11, delete "N-(2-Chloro", insert in place thereof -- N-[2-Chloro --;
Line 64, delete "-1-2-", insert in place thereof -- -1-(2- --;

Column 27,
Line 10, delete "hcat", insert in place thereof -- heat --;
Line 11, delete "IN", insert in place thereof -- 1 N --;
Line 34, delete "dimethylfornamide", insert in place thereof -- dimethylformamide --;

Column 28,
Line 11, delete "4Chloro", insert in place thereof -- 4-Chloro --;
Line 37, delete "1-2-methylpropyl)", insert in place thereof -- 1 -(2-methylpropyl) --;

Column 29,
Line 2, delete "2-Ethoxymethyl)", insert in place thereof -- 2-(Ethoxymethyl) --;
Line 47, delete "pyridin4", insert in place thereof -- pyridin-4 --;

Column 33,
Line 53, delete "(I)", insert in place thereof -- (1) --;

UNITED STATES PATENT AND TRADEMARK OFFICE
CERTIFICATE OF CORRECTION

PATENT NO. : 6,743,920 B2
DATED : June 1, 2004
INVENTOR(S) : Lindstrom, Kyle J.

It is certified that error appears in the above-identified patent and that said Letters Patent is hereby corrected as shown below:

Column 35,
Line 19, delete "C-alkyl;", insert in place thereof -- C-alkyl); --.

Signed and Sealed this

First Day of February, 2005

JON W. DUDAS
*Director of the United States Patent and Trademark Office*